(12) United States Patent
Reh et al.

(10) Patent No.: US 10,849,904 B2
(45) Date of Patent: *Dec. 1, 2020

(54) METHODS FOR TREATMENT OF RETINAL DISEASE BY PHOTORECEPTOR GENE EXPRESSION MODULATION

(71) Applicants: University of Washington, Seattle, WA (US); The J. David Gladstone Institutes, a Testamentary Trust Established Under the Will of J. David Gladstone, San Francisco, CA (US)

(72) Inventors: Thomas A. Reh, Seattle, WA (US); Paul Nakamura, Seattle, WA (US); Sheng Ding, Orinda, CA (US)

(73) Assignees: University of Washington, Seattle, WA (US); The J. David Gladstone Institutes, a Teatamentary Trust Established Under the Will of J. David. Gladstone, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/447,764

(22) Filed: Jun. 20, 2019

(65) Prior Publication Data

US 2019/0381047 A1 Dec. 19, 2019

Related U.S. Application Data

(63) Continuation of application No. 15/561,805, filed as application No. PCT/US2016/024549 on Mar. 28, 2016, now Pat. No. 10,363,256.

(60) Provisional application No. 62/139,158, filed on Mar. 27, 2015.

(51) Int. Cl.
| | |
|---|---|
| *A61K 31/519* | (2006.01) |
| *C07D 495/04* | (2006.01) |
| *A61K 31/426* | (2006.01) |
| *A61K 9/00* | (2006.01) |
| *A61P 27/02* | (2006.01) |

(52) U.S. Cl.
CPC .......... *A61K 31/519* (2013.01); *A61K 9/0048* (2013.01); *A61K 9/0051* (2013.01); *A61K 31/426* (2013.01); *A61P 27/02* (2018.01); *C07D 495/04* (2013.01)

(58) Field of Classification Search
CPC .................................................. A61K 31/519
See application file for complete search history.

(56) References Cited

U.S. PATENT DOCUMENTS 10,363,256 B2 * 7/2019 Reh ...................... A61K 31/519
2012/0278912 A1 11/2012 Farrar et al.

FOREIGN PATENT DOCUMENTS

EP 2 289 500 A1 3/2011

OTHER PUBLICATIONS

Akhmedov, N.B., et al., "A Deletion in a Photoreceptor-Specific Nuclear Receptor mRNA Causes Retinal Degeneration in the rd7 Mouse," Proceedings of the National Academy of Sciences of the United States of America 97(10):5551-5556, May 2000.
Alexander, J.J., et al., "Restoration of Cone Vision in a Mouse Model of Achromatopsia," Nature Medicine 13(6):685-687, Jun. 2007.
Bumsted O'Brien, K.M., et al., "Expression of Photoreceptor-Specific Nuclear Receptor NR2E3 in Rod Photoreceptors of Fetal Human Retina," Investigative Ophthalmology & Visual Science 45(8):2807-2812, Aug. 2004.
Carter-Dawson, L.D., and M.M. LaVail, "Rods and Cones in the Mouse Retina. I. Structural Analysis Using Light and Electron Microscopy," Journal of Comparative Neurology 188(2):242-262, 1979.
Chen, J., et al., "The Rod Photoreceptor-Specific Nuclear Receptor Nr2e3 Represses Transcription of Multiple Cone-Specific Genes," Journal of Neuroscience 25(1):118-129, Jan. 2005.
Chen, S., et al., "Crx, a Novel Otx-Like Paired-Homeodomain Protein, Binds to and Transactivates Photoreceptor Cell-Specific Genes," Neuron 19(5):1017-1030, Nov. 1997.
Cheng, H., et al., "Photoreceptor-Specific Nuclear Receptor NR2E3 Functions as a Transcriptional Activator in Rod Photoreceptors," Human Molecular Genetics 13(15):1563-1575, Aug. 2004.
Cheng, H., et al., "In Vivo Function of the Orphan Nuclear Receptor NR2E3 in Establishing Photoreceptor Identity During Mammalian Retinal Development," Human Molecular Genetics 15(17):2588-2602, Sep. 2006.
Cheng, H., et al., "Excess Cones in the Retinal Degeneration rd7 Mouse, Caused by the Loss of Function of Orphan Nuclear Receptor Nr2e3, Originate From Early-Born Photoreceptor Precursors," Human Molecular Genetics 20(21):4102-4115, Nov. 2011.
Corbo, J.C., and C.L. Cepko, "A Hybrid Photoreceptor Expressing Both Rod and Cone Genes in a Mouse Model of Enhanced S-Cone Syndrome," PLoS Genetics 1(2):e11, Aug. 2005.
Douglas, R.M., et al., "Independent Visual Threshold Measurements in the Two Eyes of Freely Moving Rats and Mice Using a Virtual-Reality Optokinetic System," Visual Neuroscience 22(5):677-684, Sep. 2005.
Diryja T.P., et al., "Mutations Within the Rhodopsin Gene in Patients With Autosomal Dominant Retinitis Pigmentosa," New England Journal of Medicine 323(19):1302-1307, Nov. 1990.
Freund, C.L., et al., "Cone-Rod Dystrophy Due to Mutations in a Novel Photoreceptor-Specific Homeobox Gene (CRX) Essential for Maintenance of the Photoreceptor," Cell 91(4):543-553, Nov. 1997.

(Continued)

*Primary Examiner* — Brian J Davis
(74) *Attorney, Agent, or Firm* — Christensen O'Connor Johnson Kindness PLLC

(57) ABSTRACT

Methods for decreasing rod gene expression in a retina, methods for decreasing the protein products expressed by rod genes in a retina, methods for treating a disease or condition treatable by decreasing rod gene expression or their protein products in a retina, and methods for treating a retinal disease in a subject.

14 Claims, 14 Drawing Sheets

(56) References Cited

OTHER PUBLICATIONS

Furukawa, T., et al., "Crx, a Novel otx-Like Homeobox Gene, Shows Photoreceptor-Specific Expression and Regulates Photoreceptor Differentiation," Cell 91(4):531-541, Nov. 1997.

Furukawa, T., et al., "Retinopathy and Attenuated Circadian Entrainment in Crx-Deficient Mice," Nature Genetics 23(4):466-470, Dec. 1999.

Hartong, D.T., et al., "Retinitis Pigmentosa," Lancet 368(9549):1795-1809, Nov. 2006.

Hennig, A.K., et al., "Regulation of Photoreceptor Gene Expression by Crx-Associated Transcription Factor Network," Brain Research 1192:114-133, Feb. 2008. (Author Manuscript provided, PMCID: PMC2266892, available in PMC Feb. 4, 2009, 34 pages).

International Search Report and Written Opinion dated Jun. 30, 2016, issued in corresponding International Application No. PCT/US2016/24549, filed Mar. 28, 2016, 7 pages.

Jaissle, G.B., et al., "Evaluation of the Rhodopsin Knockout Mouse as a Model of Pure Cone Function," Investigative Ophthalmology & Visual Science 42(2):506-513, Feb. 2001.

Kobayashi, M., et al., "Identification of a Photoreceptor Cell-Specific Nuclear Receptor," Proceedings of the National Academy of Sciences of the United States of America 96(9):4814-4819, Apr. 1999.

Koike, C., et al., "Functional Roles of Otx2 Transcription Factor in Postnatal Mouse Retinal Development," Molecular and Cellular Biology 27(23):8318-8329, Dec. 2007.

Lem, J., et al., "Morphological, Physiological, and Biochemical Changes in Rhodopsin Knockout Mice," Proceedings of the National Academy of Sciences of the United States of America 96(2):736-741, Jan. 1999.

Livesey, F.J., and C.L. Cepko, "Vertebrate Neural Cell-Fate Determination: Lessons From the Retina," Nature Reviews: Neuroscience 2(2):109-118, Feb. 2001.

Mears, A.J., et al., "Nrl is Required for Rod Photoreceptor Development," Nature Genetics 29(4):447-452, Dec. 2001.

Mitton, K.P., et al., "The Leucine Zipper of NRL Interacts With the CRX Homeodomain. A Possible Mechanism of Transcriptional Synergy in Rhodopsin Regulation," Journal of Biological Chemistry 275(38):29794-29799, Sep. 2000.

Montana, C.L., et al., "Reprogramming of Adult Rod Photoreceptors Prevents Retinal Degeneration," Proceedings of the National Academy of Sciences of the United States of America 110(5):1732-1737, Jan. 2013.

National Center for Biotechnology Information. PubChem Compound Database; CID=7901316, created Jul. 30, 2006 <https://pubchem.ncbi.nlm.nih.gov/compound/7901316> (accessed May 29, 2016), 12 pages.

National Center for Biotechnology Information. PubChem Compound Database; CID=2161722, created Jul. 14, 2005 <https://pubchem.ncbi.nlm.nih.gov/compound/2161722> (accessed May 30, 2016), 12 pages.

National Center for Biotechnology Information. PubChem Compound Database; CID=2082289, created Jul. 14, 2005 <https://pubchem.ncbi.nlm.nih.gov/compound/2082289> (accessed May 30, 2016), 12 pages.

National Center for Biotechnology Information. PubChem Compound Database; CID=24686578, created Feb. 29, 2008 <https://pubchem.ncbi.nlm.nih.gov/compound/24686578> (accessed May 29, 2016), 12 pages.

Nishida, A., et al., "Otx2 Homeobox Gene Controls Retinal Photoreceptor Cell Fate and Pineal Gland Development," Nature Neuroscience 6(12):1255-1263, Dec. 2003.

Oh, E.C., et al., "Rod Differentiation Factor NRL Activates the Expression of Nuclear Receptor NR2E3 to Suppress the Development of Cone Photoreceptors," Brain Research 1236:16-29, 2008. (Author Manuscript provided, PMCID: PMC2660138, available in PMC Oct. 21, 2009, 23 pages).

Oh, E.C.T., et al., "Transformation of Cone Precursors to Functional Rod Photoreceptors by bZIP Transcription Factor NRL," Proceedings of the National Academy of Sciences of the United States of America 104(5):1679-1684, Jan. 2007.

Pang, J.-J., et al., "Long-Term Retinal Function and Structure Rescue Using Capsid Mutant AAV8 Vector in the rd10 Mouse, A Model of Recessive Retinitis Pigmentosa," Molecular Therapy 19(2):234-242, Feb. 2011.

Peng, G.H., et al., "The Photoreceptor-Specific Nuclear Receptor Nr2e3 Interacts With Crx and Exerts Opposing Effects on the Transcription of Rod Versus Cone Genes," Human Molecular Genetics 14(6):747-764, Mar. 2005.

Pittler, S.J., et al., "Functional Analysis of the Rod Photoreceptor cGMP Phosphodiesterase Alpha-Subunit Gene Promoter: Nrl and Crx are Required for Full Transcriptional Activity," Journal of Biological Chemistry 279(19):19800-19807, May 2004.

Prusky, G.T., et al., "Rapid Quantification of Adult and Developing Mouse Spatial Vision Using a Virtual Optomotor System," Investigative Ophthalmology & Visual Science 45(12):4611-4616, Dec. 2004.

Sakami, S., et al., "Probing Mechanisms of Photoreceptor Degeneration in a New Mouse Model of the Common Form of Autosomal Dominant Retinitis Pigmentosa Due to P23H Opsin Mutations," Journal of Biological Chemistry 286(12):10551-10567, Mar. 2011.

Streichert, L.C., "A Diffusible Factor From Normal Retinal Cells Promotes Rod Photoreceptor Survival in an In Vitro Model of Retinitis Pigmentosa," Journal of Neurobiology 39(4):475-490, Jun. 1999.

Sung, C.H., et al., "Rhodopsin Mutations in Autosomal Dominant Retinitis Pigmentosa," Proceedings of the National Academy of Sciences of the United States of America 88(15):6481-6485, Aug. 1991.

Swaroop, A., et al., Transcriptional Regulation of Photoreceptor Development and Homeostasis in the Mammalian Retina, Nature Reviews: Neuroscience 11(8):563-576, Aug. 2010.

Thompson, C.B., "Apoptosis in the Pathogenesis and Treatment of Disease," Science 267(5203):1456-1462, Mar. 1995.

Turner, D.L., and C.L. Cepko, "A Common Progenitor for Neurons and Glia Persists in Rat Retina Late in Development," Nature 328(6126):131-136, Jul. 1987.

Turner, D.L., et al., "Lineage-Independent Determination of Cell Type in the Embryonic Mouse Retina," Neuron 4(6):833-845, Jun. 1990.

Wallace, V.A., "Concise Review: Making a Retina—From the Building Blocks to Clinical Applications," Stem Cells 29(3):412-417, Jan. 2011.

Webber, A.L., et al., "Dual Role of Nr2e3 in Photoreceptor Development and Maintenance," Experimental Eye Research 87(1):35-48, Jul. 2008.

Yoshida, S., et al., "Expression Profiling of the Developing and Mature Nrl-/- Mouse Retina: Identification of Retinal Disease Candidates and Transcriptional Regulatory Targets of Nrl," Human Molecular Genetics 13(14):1487-1503, May 2004.

"CID 2082289—Compound Summary," PubChem Chemical Database, No. T5260099, deposited Jul. 14, 2005, <https://pubchem.ncbi.nlm.nih.gov/compound/2082289> [retrieved May 29, 2016], 12 pages.

"CID 2161722—Compound Summary," PubChem Chemical Database, No. T5268051, deposited Jul. 14, 2005, <https://pubchem.ncbi.nlm.nih.gov/compound/2161722#section=Top> [retrieved May 29, 2016], 12 pages.

"CID 24686578—Compound Summary," PubChem Chemical Database, No. MLS001161789, deposited Feb. 29, 2008, <https://pubchem.ncbi.nlm.nih.gov/compounds/24686578#section=Top> [retrieved May 29, 2016], 12 pages.

"CID 7901316—Compound Summary," PubChem Chemical Database, No. ZINC06154146, deposited Jul. 30, 2006, <https://pubchem.ncbi.nlm.nih.gov/compound/7901316#section=Top> [retrieved May 29, 2016], 12 pages.

International Search Report and Written Opinion dated Jun. 30, 2016, issued in corresponding International Application No. PCT/US2016/024549, filed Mar. 28, 2016, 7 pages.

\* cited by examiner

CA8802

CA8803

CA8804

CA8805

CA8806

CA8807

CA8808

CA8809

CA8810

CA8811

CA8812

CA8813

CA8814

CA8815

CA8816

CA9501

CA9502

CA9503

CA9504

CA9505

CA9506

CA9507

CA9508

CA9509

CA9510

CA9511

CA9512

CA9514

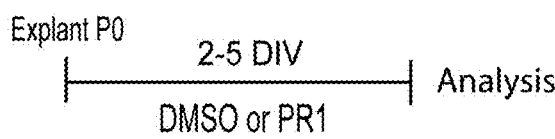
*Fig. 7A.*
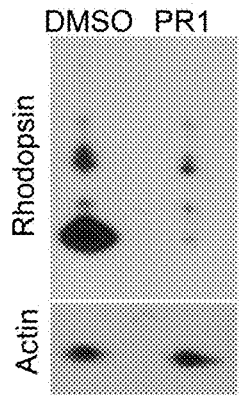
*Fig. 7B.*
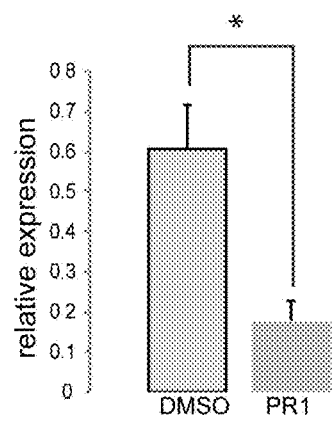
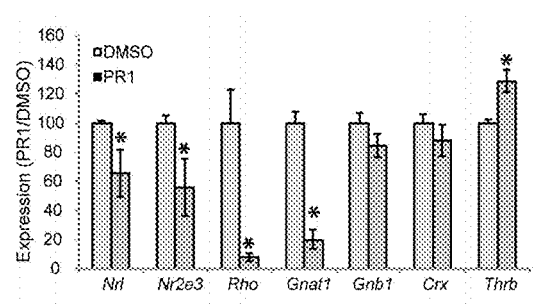
*Fig. 7D.*
*Fig. 7C.*
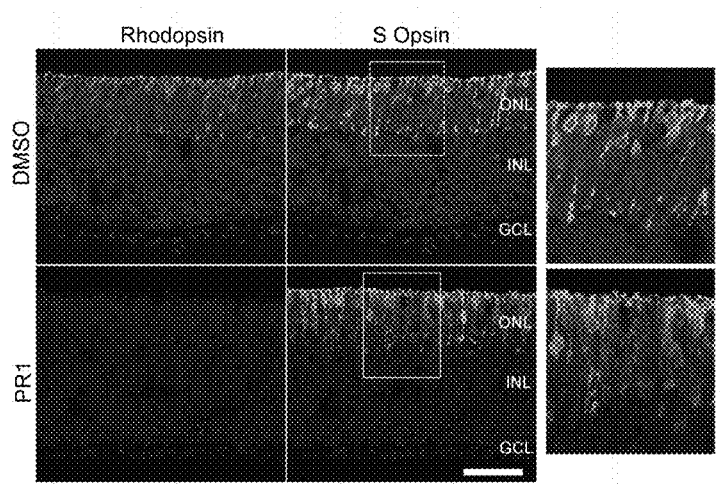
*Fig. 7E.*

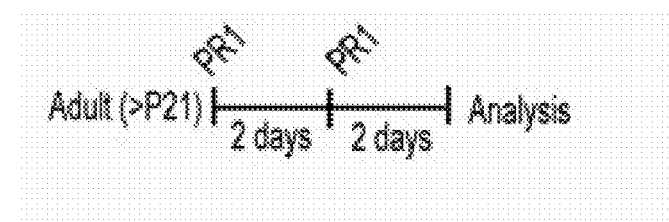
*Fig. 9A.*
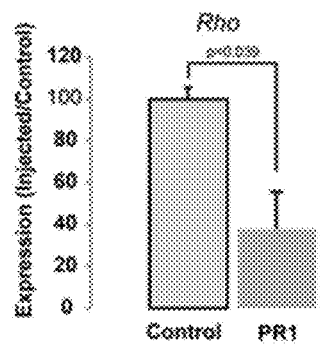
*Fig. 9B.*
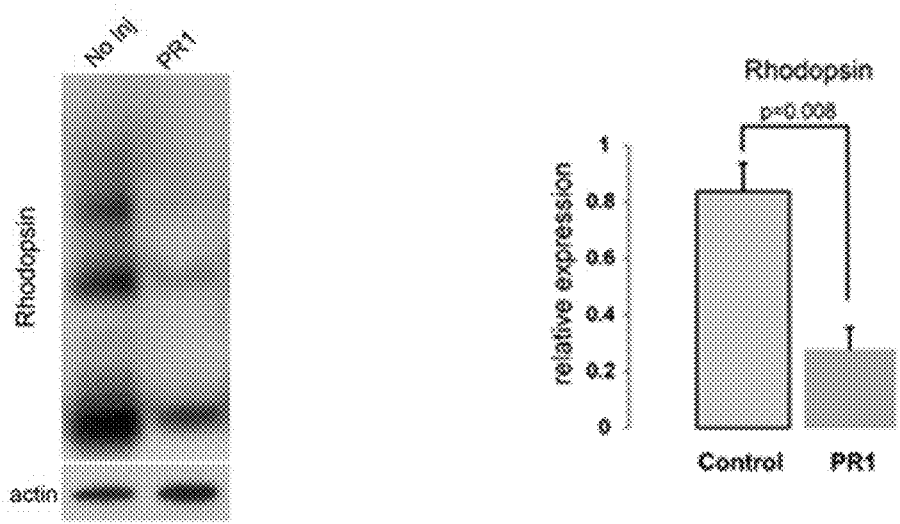
*Fig. 9C.*  *Fig. 9D.*

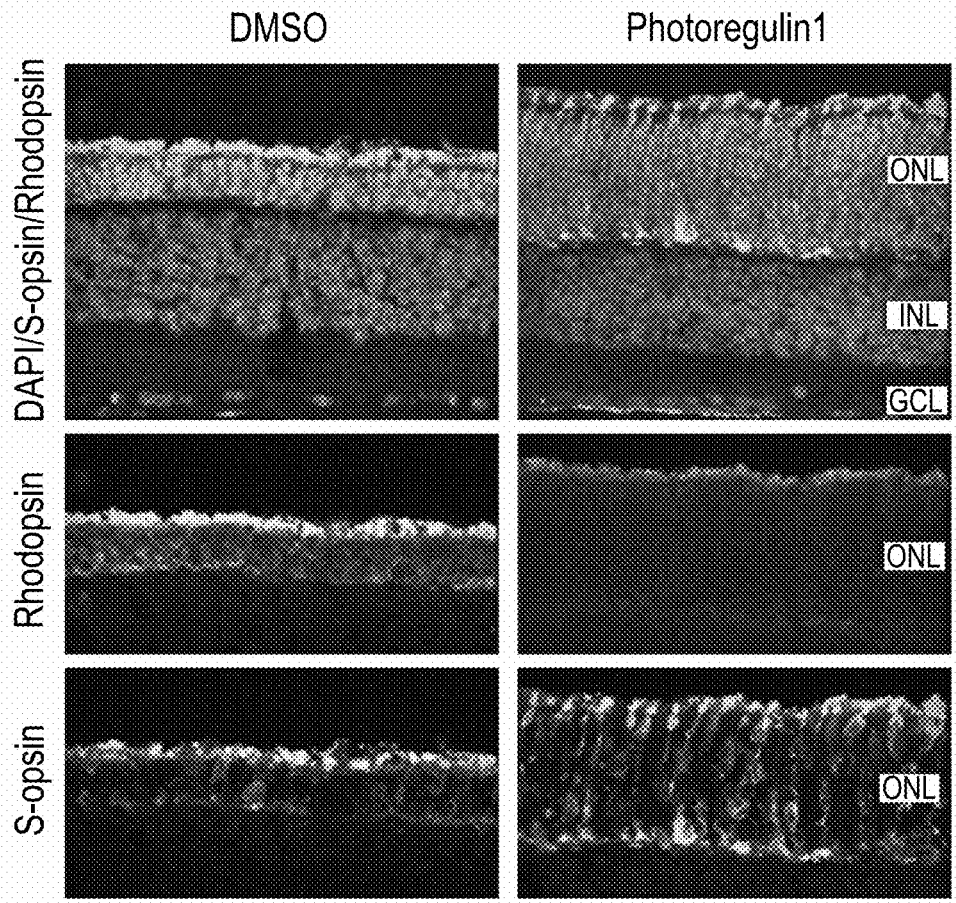
*Fig. 9H*
*Fig. 9I*
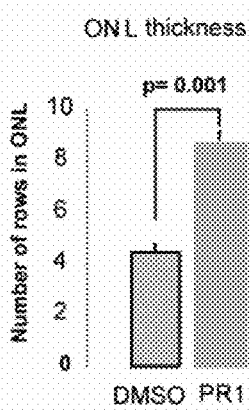
*Fig. 9J*
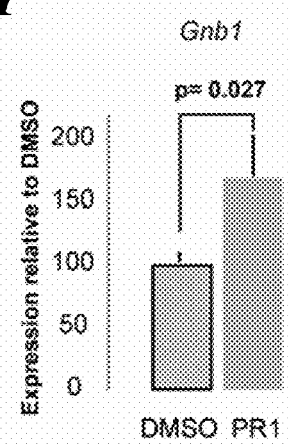
*Fig. 9K*

METHODS FOR TREATMENT OF RETINAL DISEASE BY PHOTORECEPTOR GENE EXPRESSION MODULATION

CROSS-REFERENCE TO RELATED APPLICATION

This application is a continuation of U.S. application Ser. No. 15/561,805, filed Sep. 26, 2017, which is a national stage of International Application No. PCT/US2016/024549, filed Mar. 28, 2016, which claims the benefit of U.S. Application No. 62/139,158, filed Mar. 27, 2015, each application is expressly incorporated herein by reference in its entirety.

STATEMENT OF GOVERNMENT LICENSE RIGHTS

This invention was made with Government support under Grant No. 1 RO1 EY021482 awarded by the National Institutes of Health. The Government has certain rights in the invention.

BACKGROUND OF THE INVENTION

Death of photoreceptors is a common endpoint of several retinal degenerative diseases and often eventually results in blindness. In many cases of the retinal degenerative disease retinitis pigmentosa (RP), mutations in rod photoreceptor genes result in rod photoreceptor dysfunction and subsequent cell death. The majority of mutations in Rhodopsin (RHO) that cause RP are associated with the autosomal dominant form (adRP). These mutations lead to activation of the unfolded protein response (UPR) in the rods, due to a mislocalization of the mutant protein. A number of strategies are currently being pursued to reduce the UPR in the rods, or to reduce the expression of the mutant allele using siRNA. An alternative approach to modulate rod gene expression is suggested by developmental studies. During retinal development the expression of a few key transcription factors regulates photoreceptor cell fate and further specification into rod and cone photoreceptors. One critical transcription factor in the specification of cone versus rod fate is Nrl. Mice with mutations in Nrl have a retina without rods, but an increase in the number of cones because the rod precursors become cones without the expression of Nrl. Conversely, overexpression of Nrl in cone precursors results in decreased cone gene expression and a transformation to rod photoreceptors.

A recent study showed that partial transdifferentiation of mature rods into cones by conditional knockout of Nrl can prevent retinal degeneration in a mouse model of recessive RP (Rho$^{-/-}$ mice). This reprogramming of rods into cone-like cells prevented their death and therefore any secondary cone cell death as well. The orphan nuclear receptor Nr2e3 (also known as photoreceptor nuclear receptor) is a direct target of Nrl and is expressed in postmitotic photoreceptors soon after the onset of Nrl expression. Nr2e3 has a dual role as a transcriptional suppressor and co-activator during retinal development. It is required for the suppression of cone gene expression, as evidenced by the findings that mice with targeted or spontaneous mutations in Nr2e3 have increased expression of cone genes in rod-like photoreceptors. Additionally, Nr2e3 co-activates the transcription of rod-specific genes like Rho and Gnat1 along with Crx and Nrl.

The finding that partial reprogramming of rods to cones can reduce rod death and decrease secondary cone loss to spare cone-mediated vision in a mouse model of RP provides an approach to develop therapies for this disorder and other similar degenerative diseases. This pathway is also potentially amenable to manipulation pharmacologically, since Nr2e3, the downstream target of Nrl, is a nuclear hormone receptor, and probably capable of antagonism.

Despite the advances for treating retinal disease, a need exists for improved therapeutic agents and treatments. The present invention seeks to fulfill this need and provides further related advantages.

SUMMARY OF THE INVENTION

The present invention provides methods for decreasing rod gene expression in a retina, methods for decreasing the protein products expressed by rod genes in a retina, methods for treating a disease or condition treatable by decreasing rod gene expression or their protein products in a retina, and methods for treating a retinal disease in a subject.

In one aspect, the invention provides a method for decreasing rod gene expression in a retina.

In one embodiment, the method includes contacting a retina with a compound having formula (I):

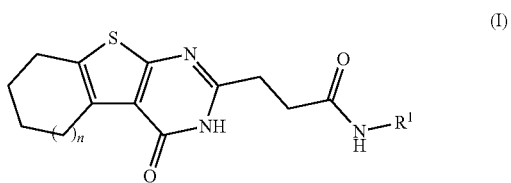

(I)

or a pharmaceutically acceptable salt thereof, wherein $R^1$ is phenyl substituted with one or two groups independently selected from the group consisting of C1-C6 alkyl and halogen, and n is 0 or 1.

In another embodiment, the method includes contacting a retina with a compound having formula (II):

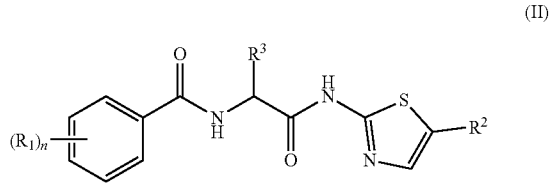

(II)

or a pharmaceutically acceptable salt thereof, wherein $R^1$ is independently at each position a C1-C6 alkyl group, $R^2$ is selected from the group consisting of hydrogen and C1-C6 alkyl, $R^3$ is selected from the group consisting of hydrogen and C1-C6 alkyl, and n is 0, 1, or 2.

In another aspect, the invention provides a method for reducing the expression of protein products derived from rod genes. In certain embodiments, the invention provides a method for decreasing rhodopsin expression in a retina. In one embodiment of this method, a retina is treated with a compound having formula (I) or a pharmaceutically acceptable salt thereof. In another embodiment of this method, a retina is treated with a compound having formula (II) or a pharmaceutically acceptable salt thereof.

In a further aspect of the invention, methods are provided for treating a disease or condition treatable by decreasing rod gene expression, or their protein products, in a retina. In certain embodiments, the methods include administering to a subject in need thereof a therapeutically effective amount of a compound having formula (I) or a pharmaceutically acceptable salt thereof. In other embodiments, the method includes administering to a subject in need thereof a therapeutically effective amount of a compound having formula (II) or a pharmaceutically acceptable salt thereof.

Representative diseases or conditions treatable by decreasing rod gene expression, or their protein products, in a retina include retinitis pigmentosa, retinal degeneration, macular degeneration, age-related macular degeneration, Stargardt's macular dystrophy, retinal dystrophy, Sorsby's fundus dystrophy, diabetic retinopathy, diabetic maculopathy, retinopathy of prematurity, and ischemia reperfusion related retinal injury. In one embodiment, the treatable disease or condition is retinitis pigmentosa.

In another aspect, the invention provides methods for treating a retinal disease in a subject. In certain embodiments, the methods include administering to a subject in need thereof a therapeutically effective amount of a compound having formula (I) or a pharmaceutically acceptable salt thereof. In other embodiments, the method includes administering to a subject in need thereof a therapeutically effective amount of a compound having formula (II) or a pharmaceutically acceptable salt thereof. Representative retinal diseases treatable by the methods of the invention include retinitis pigmentosa, retinal degeneration, macular degeneration, age-related macular degeneration, Stargardt's macular dystrophy, retinal dystrophy, Sorsby's fundus dystrophy, diabetic retinopathy, diabetic maculopathy, retinopathy of prematurity, and ischemia reperfusion related retinal injury. In one embodiment, the treatable disease or condition is retinitis pigmentosa.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

FIGS. 7A-7J. Schematic for experimental design for panels 7B-7E (7A). Western blot for rhodopsin shows significant reduction in P0 explants treated with 1 µM PR1 for 5 DIV (7B). Rhodopsin expression was normalized to β-actin; PR1-treated explants had less relative expression than DMSO controls (n=4, *p<0.05, Student's t-test) (7C). RT-qPCR for P0 explants treated with DMSO or 1 µM PR1 for 2 DIV; Nrl, Nr2e3, rhodopsin, and Gnat1 were significantly reduced with PR1, while Gnb1 and Crx did not change; the expression of the cone gene Thrb was increased in PR1-treated explants (n=3, *p<0.05, Student's t-test) (7D). Sections from DMSO and 1 µM PR1 treated P0 explants stained for rhodopsin and S opsin demonstrate a decrease in rhodopsin+ cells and an increase in S opsin+ cells; scale bar represents 50 µm (7E). Schematic for experimental design for panels 7G and 7H (7F). Timed-pregnant dams were injected with 100 µl of 50 mM PR1 at E14 and E17 and pups were sacrificed for analysis at P0; PR1 treated pups had more S opsin+ cells per 200 µm of central retina compared to controls (n≥6 retinas from 3 animals; *p<0.05, Student's t-test) (7G). Sections of central retina from control and PR1 pups stained for S opsin; scale bar represents 50 µm (7H). Schematic for experimental design for panel J (7I). Postnatal pups were IP injected with DMSO or 20 µL of 50 mM PR1 at P2 or P3 and then sacrificed 24 hours later for RT-qPCR analysis; PR1 decreased rhodopsin expression in P2-3 pups (n=4-5; *p<0.05, Student's t-test) (7J).

FIGS. 9A-9K. Schematic for experimental design for panels 9B-9D (9A). Adult mice received two 1.5 µL intravitreal injections of 10 mM PR1 into one eye over a 4 day paradigm; compared to the control retina, PR1 decreased rhodopsin expression in adult retinas (n=3, *p<0.05, Student's t-test) (9B). Western blot for rhodopsin shows that intravitreal injection of PR1 decreases expression compared to the uninjected, contralateral retina of adult mice (9C). Rhodopsin expression was normalized to β-actin expression. PR1 decreased the relative expression of rhodopsin after intravitreal injection in adult mice (n=5, *p<0.05, Student's t-test) (9D). Schematic for experimental design for panels 9F and 9G (9E). Retinas from P8 Rho$^{P23H}$ mice were explanted in DMSO or 2 µM PR1 for 3 DIV; Western blot analysis shows that PR1 treated Rho$^{P23H}$ retinas have less mutant rhodopsin expression than DMSO controls (9F). Rhodopsin expression was normalized to β-actin expression; PR1 Rho$^{P23H}$ retinas had less relative expression of rhodopsin than DMSO-treated Rho$^{P23H}$ controls (n=3, *p<0.05, Student's t-test) (9G). Schematic for experimental design for panels 9I-9K (9H). Retinas from P12 Rho$^{P23H}$ mice were explanted in DMSO or 1 μM PR1 for 6 DIV; DAPI staining demonstrates that PR1 treated Rho$^{P23H}$ retinas had thicker ONLs in the central retina compared to DMSO treated Rho$^{P23H}$ retinas (9I). Quantification of DAPI+ cells in the ONL 100 μm from the optic nerve head in DMSO and PR1 treated Rho$^{P23H}$ retinas (n=3, *p<0.05, Student's t-test) (9J). RT-qPCR analysis of Gnb1 expression in DMSO and PR1 Rho$^{P23H}$ retinas suggests greater rod survival with PR1 treatment, since PR1 does not affect expression of this rod-specific transcript (n=3, *p<0.05, Student's t-test) (9K).

DETAILED DESCRIPTION OF THE INVENTION

The present invention provides methods for decreasing rod gene expression in a retina, methods for decreasing the protein products (e.g., rhodopsin) expressed by rod genes in a retina, methods for treating a disease or condition treatable by decreasing rod gene expression or their protein products in a retina, and methods for treating a retinal disease in a subject. In the methods, the retina or subject are treated with select small molecules to achieve the advantageous result of decreasing rod gene expression, thereby decreasing the expression of their protein products, and consequently treating a disease or condition treatable by decreasing rod gene expression or their protein products. The select small molecules are effective for treating retinal diseases such as retinitis pigmentosa (RP).

Decreasing Rod Gene Expression and their Protein Products

In one aspect, the invention provides a method for decreasing rod gene expression in a retina.

In one embodiment, the method includes contacting a retina with a compound having formula (I):

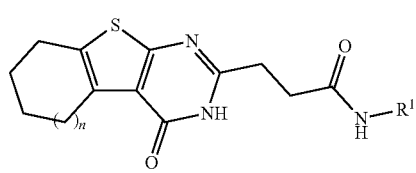

(I)

or a pharmaceutically acceptable salt thereof, wherein R$^1$ is phenyl substituted with one or two groups independently selected from the group consisting of C1-C6 alkyl and halogen, and n is 0 or 1.

As used herein the C1-C6 alkyl refers to straight chain, branched, and cycloalkyl groups. Representative alkyl groups include methyl, ethyl, n-propyl, i-propyl, n-butyl, n-pentyl, and n-hexyl groups; and cyclopropyl, cyclobutyl, cyclopentyl, and cyclohexyl groups.

The term "halogen" includes fluoro, chloro, and bromo groups.

In certain embodiments, the compound of formula (I) includes a single alkyl group (e.g., methyl, ethyl, i-propyl). In other embodiments, the compound of formula (I) includes a single halogen group (e.g., fluoro or bromo).

In certain embodiments, the compound of formula (I) includes two alkyl groups (e.g., dimethyl). In other embodiments, the compound of formula (I) includes an alkyl group and a halogen group (e.g., methyl and bromo). In further embodiments, the compound of formula (I) includes two halogen groups (e.g., difluoro).

The compounds of formula (I) can be prepared by the following synthetic reaction scheme:

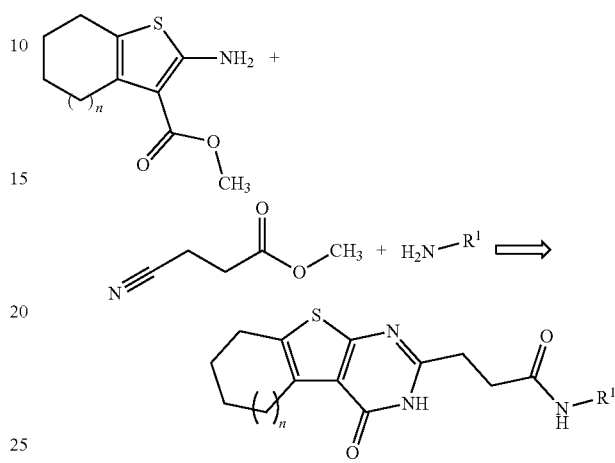

In certain embodiments, the compound of formula (I) is CA88:

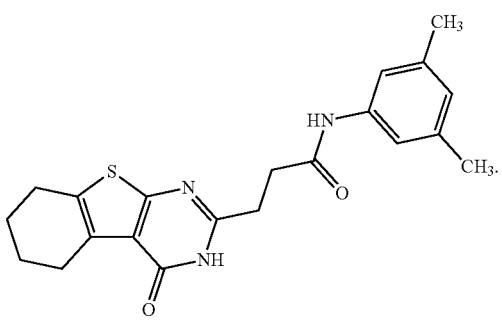 [SMILES: Cc1cc(C)cc(NC(=O)CCc2nc3sc4c(c3c(=O)[nH]2)CCCC4)c1]

In other embodiments, the compound of formula (I) is CA8801:

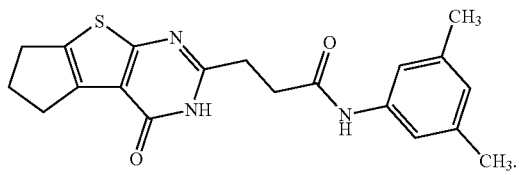 [SMILES: Cc1cc(C)cc(NC(=O)CCc2nc3sc4c(c3c(=O)[nH]2)CCC4)c1]

Compounds CA88 and CA8801 are commercially available from ChemDiv (San Diego, Calif.).

Figure 1:
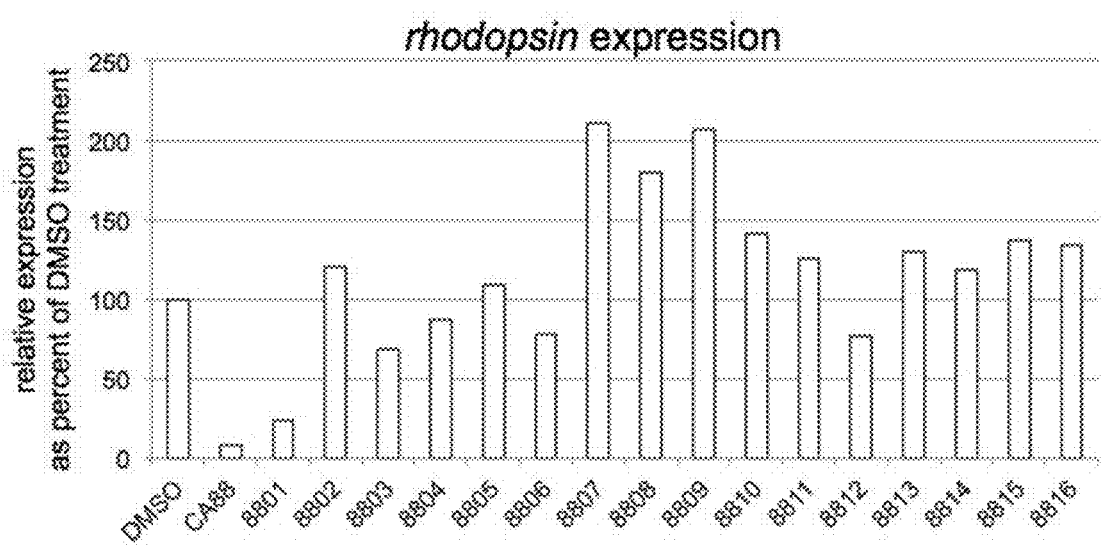
FIG. 1 compares relative rhodopsin expression of intact retinas from P12 wild type mice explanted in media containing DMSO, CA88 and CA8801-8816 at 1 µM for 2 days and then processed for qPCR.
Figure 2:
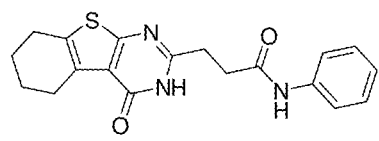
FIG. 2 illustrates the chemical structures of analogs CA8802-CA8816.
Figure 2:
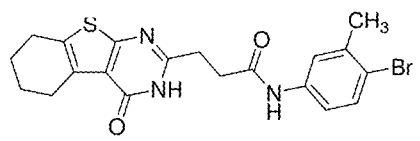
Figure 2:
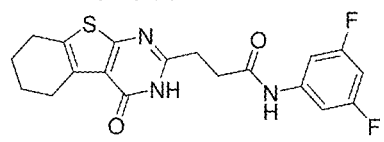
Figure 2:
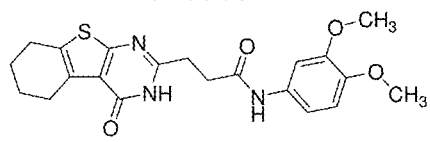
Figure 2:
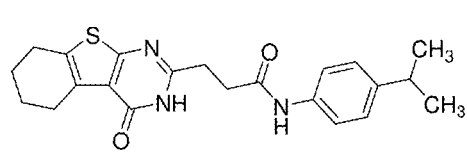
Figure 2:
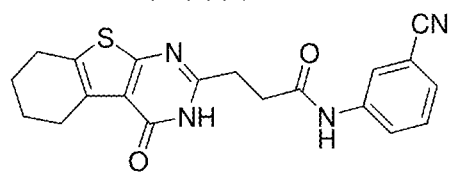
Figure 2:
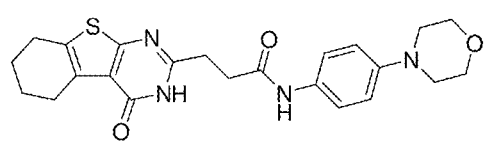
Figure 2:
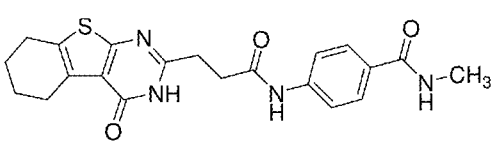
Figure 2:
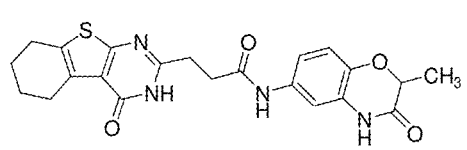
Figure 2:
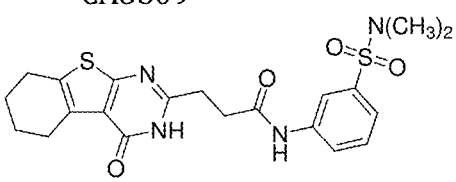
Figure 2:
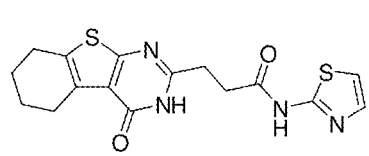
Figure 2:
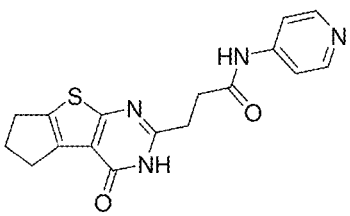
Figure 2:
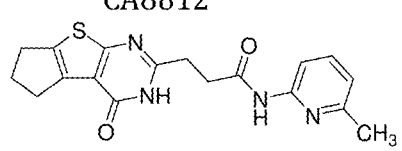
Figure 2:
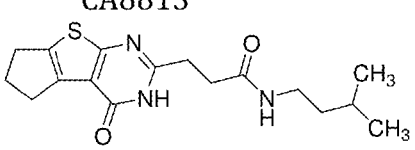
Figure 2:
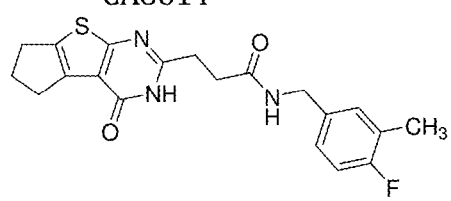

Rod genes whose expression are effectively reduced in the practice of the methods of the invention include Nrl, Nr2e3, Rho, Gnat1, and Pde6b. The effectiveness of CA88 and CA8801 in reducing rhodopsin expression in intact retinas from P12 wild type mice explanted in media at 1 uM for 2 days is shown in FIG. 1. FIG. 1 compares relative rhodopsin expression for CA88 and CA8801 to dimethylsulfoxide (control) and related analogs 8802-8816. The chemical structures of analogs 8802-8816 are shown in FIG. 2.

In another embodiment, the method includes contacting a retina with a compound having formula (II):

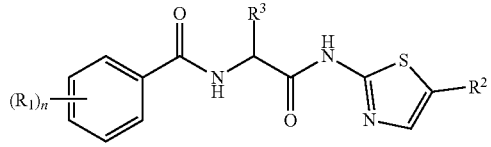

or a pharmaceutically acceptable salt thereof, wherein $R^1$ is independently at each position a C1-C6 alkyl group, $R^2$ is selected from the group consisting of hydrogen and C1-C6 alkyl, $R^3$ is selected from the group consisting of hydrogen and C1-C6 alkyl, and n is 0, 1, or 2. C1-C6 alkyl is as described above for the compounds of formula (I). $R^1$ may be a substituent at any carbon of the phenyl group.

In certain embodiments, the compounds of formula (II) have $R^1$ selected from C1-C4 alkyl (e.g., methyl), n=1, $R^2$ selected from hydrogen and C1-C4 alkyl (e.g., i-propyl), and $R^3$ selected from C1-C4 alkyl (e.g., methyl). In one embodiment, $R^1$ is methyl, n=1, $R^2$ is i-propyl, and $R^3$ is methyl). In another embodiment, $R^1$ is methyl, n=1, $R^2$ is hydrogen, and $R^3$ is methyl.

The compounds of formula (II) can be prepared by the following synthetic reaction scheme:

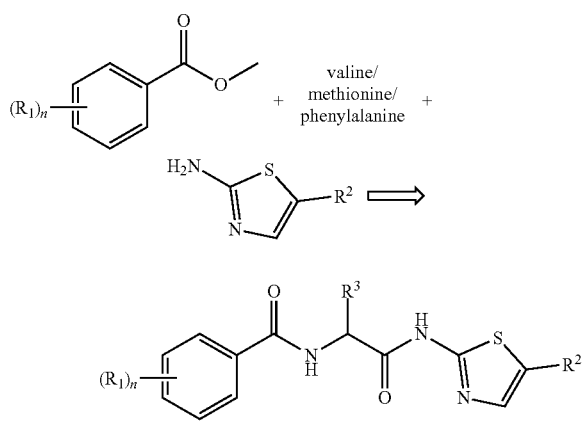

In certain embodiments, the compound of formula (II) is CA95:

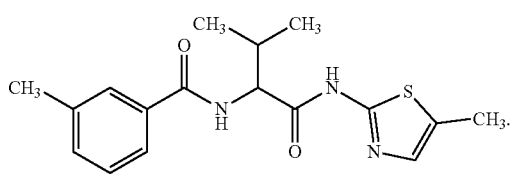 [SMILES: Cc1cccc(C(=O)NC(C(=O)Nc2ncc(C)s2)C(C)C)c1]

In other embodiments, the compound of formula (II) is CA9513:

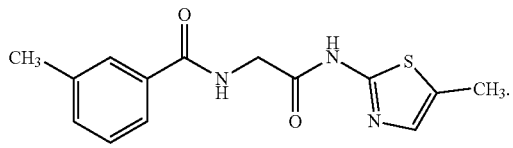 [SMILES: Cc1cccc(C(=O)NCC(=O)Nc2ncc(C)s2)c1]

Compounds CA95 and CA9513 are commercially available from ChemDiv (San Diego, Calif.).

Figure 3:
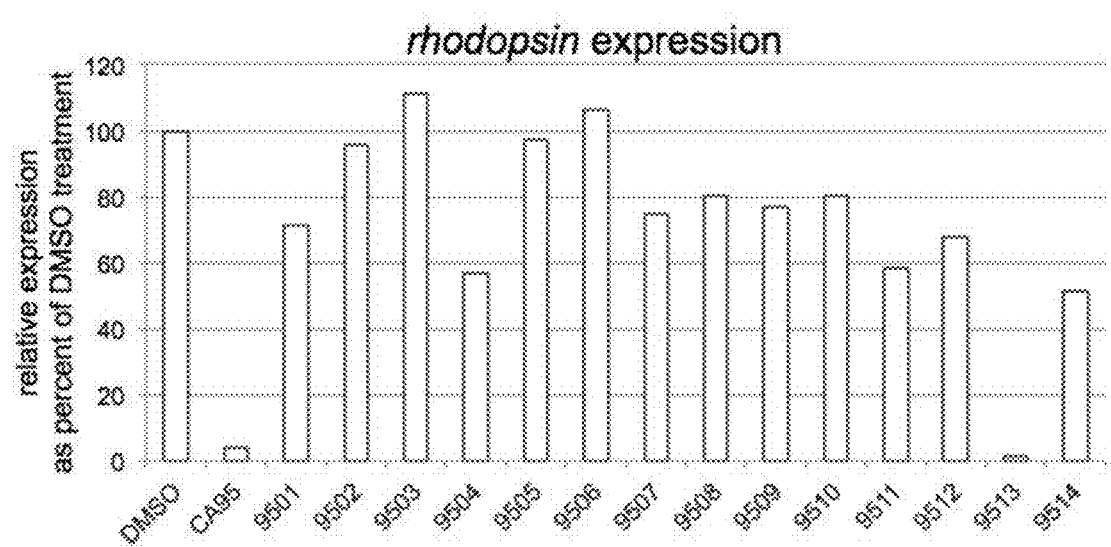
FIG. 3 compares relative rhodopsin expression of intact retinas from P12 wild type mice explanted in media containing DMSO, CA95 and CA9501-9514 at 1 µM for 2 days and then processed for qPCR.
Figure 4:
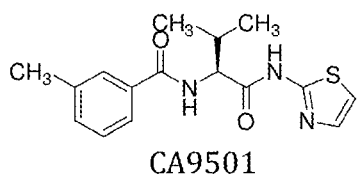
FIG. 4 illustrates the chemical structures of analogs CA9501-CA9512 and CA9514.
Figure 4:
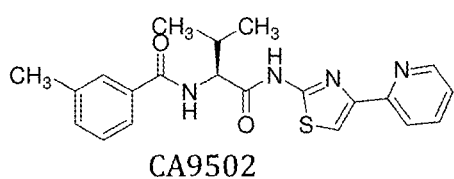
Figure 4:
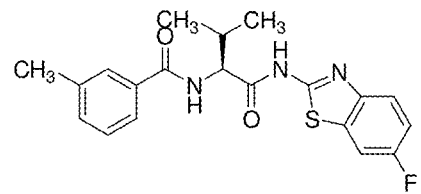
Figure 4:
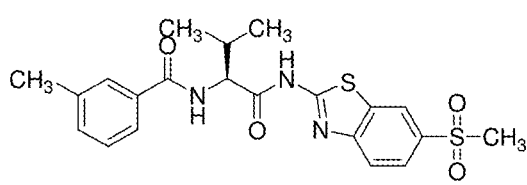
Figure 4:
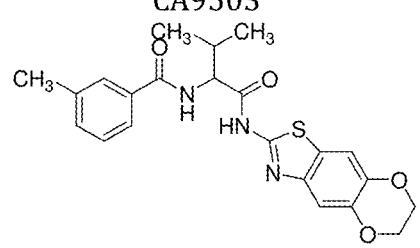
Figure 4:
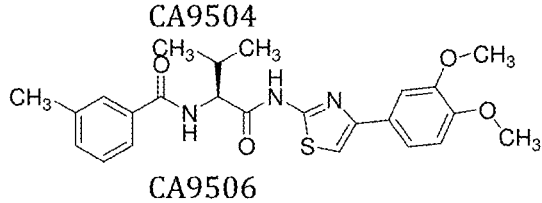
Figure 4:
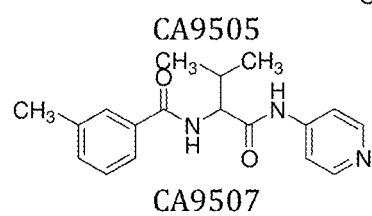
Figure 4:
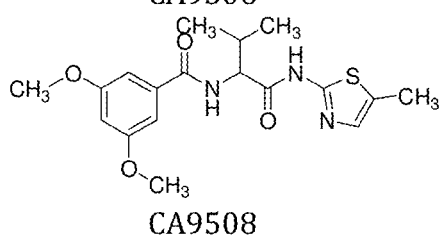
Figure 4:
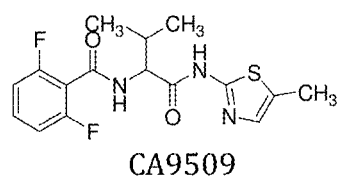
Figure 4:
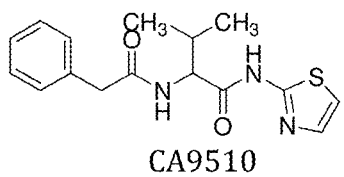
Figure 4:
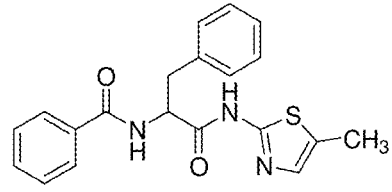
Figure 4:
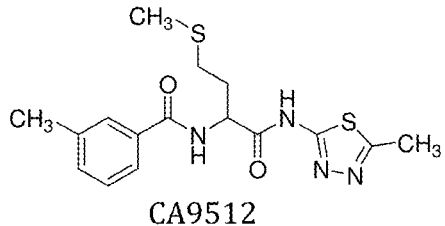
Figure 4:
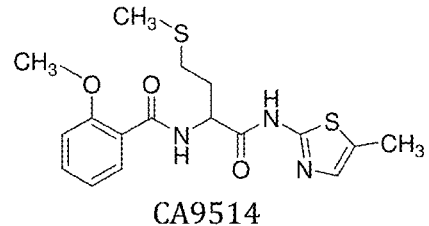

Rod genes whose expression are effectively reduced in the practice of the invention include Nrl, Nr2e3, Rho, and Gnat1. The effectiveness of CA95 and CA9513 in reducing rhodopsin expression in intact retinas from P12 wild type mice explanted in media at 1 uM for 2 days is shown in FIG. 3. FIG. 3 compares relative rhodopsin expression for CA95 and CA9513 to dimethylsulfoxide (control) and related analogs 9501-9512 and 9514. The chemical structures of analogs 9501-9512 and 9514 are shown in FIG. 4.

In certain embodiments of the above methods, contacting the retina comprises systemic administration of the compound to the subject or intravitreal injection of the compound.

In another aspect, the invention provides a method for reducing the expression of protein products derived from rod genes. In certain embodiments, the invention provides a method for decreasing rhodopsin expression in a retina.

In one embodiment of this method, a retina is treated with a compound having formula (I) or a pharmaceutically acceptable salt thereof, as described above. In certain of these embodiments, the compound of formula (I) is CA88. In other of these embodiments, the compound of formula (I) is CA8801.

In another embodiment of this method, a retina is treated with a compound having formula (II) or a pharmaceutically acceptable salt thereof, as described above. In certain of these embodiments, the compound of formula (II) is CA95. In other of these embodiments, the compound of formula (II) is CA9513.

In certain embodiments of the above methods, treating the retina comprises systemic administration of the compound to the subject or intravitreal injection of the compound.

Treating Diseases or Conditions Treatable by Decreasing Rod Gene Expression or their Protein Products In a further aspect of the invention, methods are provided for treating a disease or condition treatable by decreasing rod gene expression, or their protein products, in a retina.

In certain embodiments, the methods include administering to a subject in need thereof a therapeutically effective amount of a compound having formula (I) or a pharmaceutically acceptable salt thereof, as described above. In certain of these embodiments, the compound of formula (I) is CA88. In other of these embodiments, the compound of formula (I) is CA8801.

In other embodiments, the method includes administering to a subject in need thereof a therapeutically effective amount of a compound having formula (II) or a pharmaceutically acceptable salt thereof, as described above. In certain of these embodiments, the compound of formula (II) is CA95. In other of these embodiments, the compound of formula (II) is CA9513.

Representative diseases or conditions treatable by decreasing rod gene expression, or their protein products, in a retina include retinitis pigmentosa, retinal degeneration, macular degeneration, age-related macular degeneration, Stargardt's macular dystrophy, retinal dystrophy, Sorsby's fundus dystrophy, diabetic retinopathy, diabetic maculopathy, retinopathy of prematurity, and ischemia reperfusion related retinal injury. In one embodiment, the treatable disease or condition is retinitis pigmentosa.

In certain embodiments of the above methods, administering the compound comprises systemic administration of the compound to the subject or intravitreal injection of the compound.

Treating Retinal Disease

In another aspect, the invention provides methods for treating a retinal disease in a subject.

In certain embodiments, the methods include administering to a subject in need thereof a therapeutically effective amount of a compound having formula (I) or a pharmaceutically acceptable salt thereof, as described above. In certain of these embodiments, the compound of formula (I) is CA88. In other of these embodiments, the compound of formula (I) is CA8801.

In other embodiments, the method includes administering to a subject in need thereof a therapeutically effective amount of a compound having formula (II) or a pharmaceutically acceptable salt thereof, as described above. In certain of these embodiments, the compound of formula (II) is CA95. In other of these embodiments, the compound of formula (II) is CA9513.

Representative retinal diseases treatable by the methods of the invention include retinitis pigmentosa, retinal degeneration, macular degeneration, age-related macular degeneration, Stargardt's macular dystrophy, retinal dystrophy, Sorsby's fundus dystrophy, diabetic retinopathy, diabetic maculopathy, retinopathy of prematurity, and ischemia reperfusion related retinal injury. In one embodiment, the treatable disease or condition is retinitis pigmentosa.

In certain embodiments of the above methods, administering the compound comprises systemic administration of the compound to the subject or intravitreal injection of the compound.

In the methods of the invention that are methods of treatment, the term "therapeutically effective amount" refers to an amount effective, at dosages and for periods of time necessary, to achieve the desired therapeutic result, such as reduced levels of rod gene expression or their protein products. A therapeutically effective amount of a compound may vary according to factors such as the disease state, age, sex, and weight of the subject, and the ability of the compound to elicit a desired response in the subject. Dosage regimens can be adjusted to provide the optimum therapeutic response. A therapeutically effective amount is also one in which any toxic or detrimental effects of the administered compound are outweighed by the therapeutically beneficial effects.

It is to be noted that dosage values can vary with the severity of the condition to be alleviated. For any particular subject, specific dosage regimens can be adjusted over time according to the individual need and the professional judgment of the person administering or supervising the administration of the compositions. Dosage ranges set forth herein are exemplary only and do not limit the dosage ranges that can be selected by a medical practitioner. The amount of active compound in the composition can vary according to factors such as the disease state, age, sex, and weight of the subject. Dosage regimens can be adjusted to provide the optimum therapeutic response. For example, a single bolus can be administered, several divided doses can be administered over time or the dose can be proportionally reduced or increased as indicated by the exigencies of the therapeutic situation.

In the methods, the administration of the compound can be a local administration (e.g., administration to the eye), or systemic administration to the subject. The term "subject" is intended to include mammalian organisms. Examples of subjects include humans and non-human mammals. In specific embodiments of the invention, the subject is a human.

The terms "administering," "contacting," or "treating" include any method of delivery of a compounds or a pharmaceutical composition comprising the compound into a subject's system or to a particular region of the subject (e.g., eye).

Increasing Cone Gene Expression Methods

In further aspects, the invention provides methods for increasing cone gene expression, or their protein products, in a retina.

In one embodiment of this method, a retina is treated or contacted with a compound having formula (I) or a pharmaceutically acceptable salt thereof, as described above. In certain of these embodiments, the compound of formula (I) is CA88. In other of these embodiments, the compound of formula (I) is CA8801.

In another embodiment of this method, a retina is treated or contacted with a compound having formula (II) or a pharmaceutically acceptable salt thereof, as described above. In certain of these embodiments, the compound of formula (II) is CA95. In other of these embodiments, the compound of formula (II) is CA9513.

In certain embodiments of the above methods, treating or contacting the retina comprises systemic administration of the compound to the subject or intravitreal injection of the compound.

Cone genes whose expression that are effectively increased in the practice of the invention include M Ops, S Ops, Gnat2, Gnb3, Rxrg, Trβ2, and Pde6h.

In a related aspect, the invention provides a method for increasing Trβ2 expression in a retina.

In one embodiment of this method, a retina is treated or contacted with a compound having formula (I) or a pharmaceutically acceptable salt thereof, as described above. In certain of these embodiments, the compound of formula (I) is CA88. In other of these embodiments, the compound of formula (I) is CA8801.

In another embodiment of this method, a retina is treated or contacted with a compound having formula (II) or a pharmaceutically acceptable salt thereof, as described above. In certain of these embodiments, the compound of formula (II) is CA95. In other of these embodiments, the compound of formula (II) is CA9513.

Figure 5:
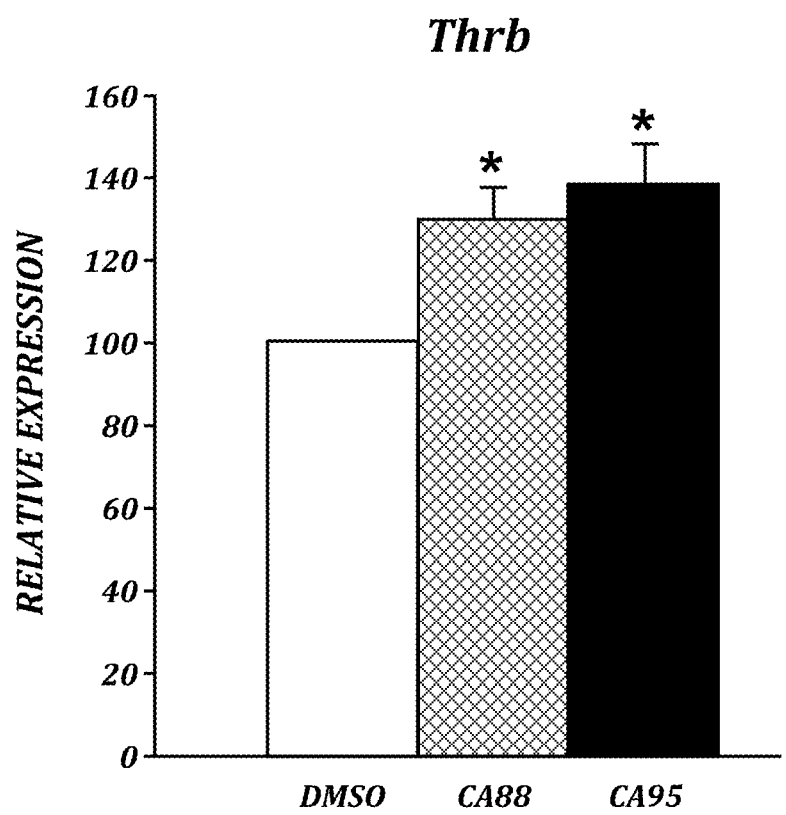
FIG. 5 compares cone gene expression increase for Thrb (TRβ2) with CA88 and CA95.

FIG. 5 compares cone gene expression increase for Thrb (Trβ2) with CA88 and CA95.

In certain embodiments of the above methods, treating or contacting the retina comprises systemic administration of the compound to the subject or intravitreal injection of the compound.

Pharmaceutical Compositions

In another aspect, the invention provides a pharmaceutical composition that includes a pharmaceutically acceptable carrier and a compound having formula (I) or formula (II) or a pharmaceutically acceptable salt thereof, are described above. In certain embodiments, the compound is CA88, CA8801, CA95, or CA9513.

Suitable carriers include those suitable for administration to an animal (e.g., a human subject). Pharmaceutical compositions suitable for injectable use include sterile aqueous solutions (e.g., saline, dextrose) and dispersions.

The compositions of the invention can be orally administered, for example, with an inert diluent or carrier, enclosed in hard or soft shell gelatin capsule, or compressed into tablets. For oral therapeutic administration, the compounds and compositions can be combined with excipients and used in the form of ingestible tablets, buccal tables, troches, capsules, elixirs, suspensions, syrups, wafers, and the like. The amount of active compounds in such therapeutically useful compositions is such that a suitable dosage is obtained.

The compounds and compositions of the invention can be administered parenterally. Solutions of the compounds as free base or pharmacologically acceptable salts can be prepared in water suitably mixed with additives, such as surfactants. Dispersions can also be prepared in oils.

The following description relates to a small molecule antagonist of Nr2e3a useful in the methods of the invention. More particularly, the following describes small molecule reprogramming of rod photoreceptors to treat retinitis pigmentosa (RP).

As described herein, small molecule antagonists of Nr2e3 have been identified using intact developing retinas and these compounds have significant and selective effects on rod gene expression. On such putative Nr2e3 antagonist is N-(3,5-dimethylphenyl)-3-(4-oxo-5,6,7,8-tetrahydro-3H-[1]benzothiolo[2,3-d]pyrimidin-2-yl)propanamide, referred to herein is as "CA88" or "Photoregulin1" or "PR1." PR1 was found to decrease the expression of rod genes and increased the number of S opsin+ cones. PR1 also slowed degeneration of photoreceptors in an in vitro model of RP, providing evidence that chemical probes targeted against Nr2e3 may be therapeutically useful for the treatment of retinal degenerative diseases.

Screen of Putative Chemical Probes of Nr2e3 with Intact Retinal Explant Cultures.

Figure 6A:
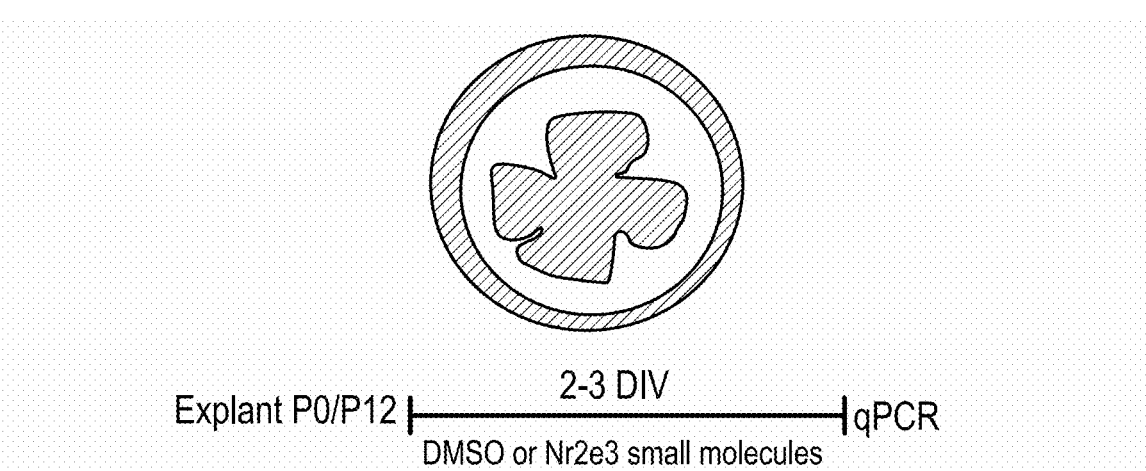
FIGS. 6A-6E. Schematic showing experimental design for screen of small molecules (6A). RT-qPCR for rod photoreceptor genes expressed in DMSO treated controls and 1 µM PR1 treated retinal explants from P12 mice for 3 DIV (n=4; *p<0.05) (6B) Dose-response relationship of PR1 on rod specific genes Nrl, Nr2e3, and rhodopsin in P12 retinal explants (n=3-4) (6C). Human retinal explants from 113 day post-conception fetuses were cultured in media with DMSO or 10 µM PR1 for 7 or 23 days; PR1 treatment decreased normalized RHO expression after 7 and 23 days in culture (6D). HEK293T cells were transfected with NR2E3, CRX, or NRL and BR-225Luc (firefly luciferase driven by the bovine rhodopsin promoter) and pRL-CMV (renilla luciferase driven by the CMV promoter; internal transfection control) and then treated with DMSO or 10 µM PR1 for 2 days; PR1 decreased rhodopsin promoter activity after transfection with Crx and Nrl and transfection with Nr2e3, Crx, and Nrl (n≥3; *p<0.05, Student's t-test) (6E).
Figure 6B:
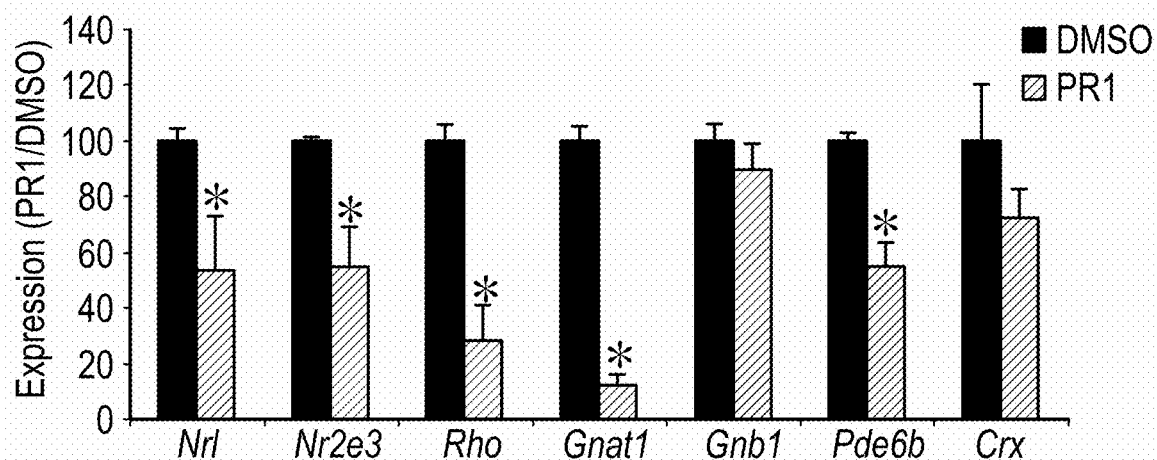

To identify functional Nr2e3 antagonists, compounds were cheminformatically searched and structural analogs of a putative Nr2e3 interacting compound with unknown function were collected. See FIGS. 2 and 4 for the structures of the compounds. The collected compounds were then screened in a physiologically relevant primary culture assay using intact retinas from postnatal day 12-13 (P12-13) C57BL/6 mice for suppression of Rho expression (See FIG. 6A). After a 2 day culture period with media containing DMSO or compounds at 1 µM, the retinas were collected and assessed Rho expression by qPCR. Rho was chosen because it is a well-described target of Nr2e3 in rod photoreceptors. Photoregulin1 (PR1) was found to substantially decrease Rho expression compared to DMSO in retinal explants from P12-13 mice (FIG. 6B). This analysis also provided an initial structure-activity relationship.

Figure 6C:
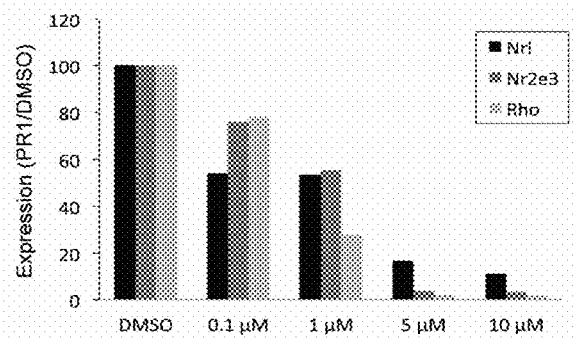
Figure 6D:
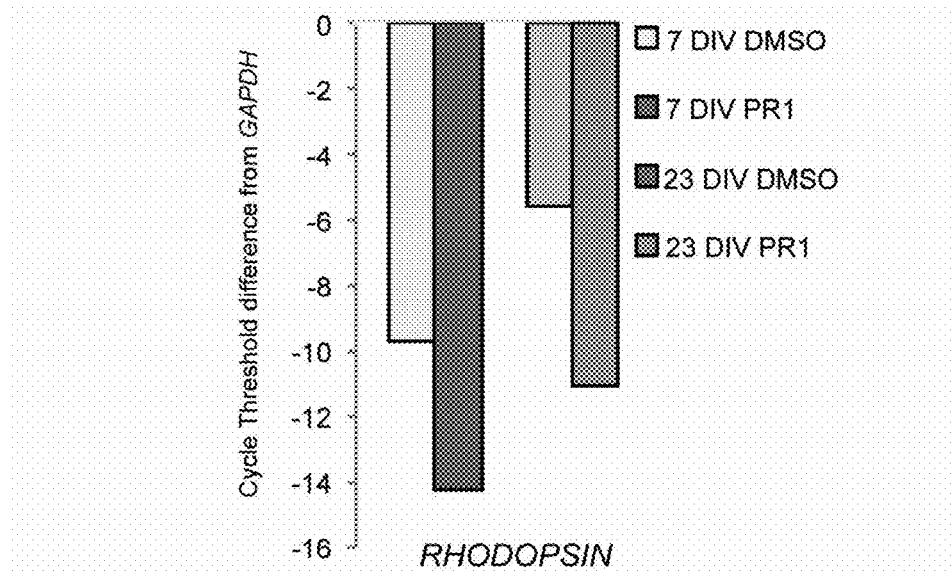
Figure 6E:
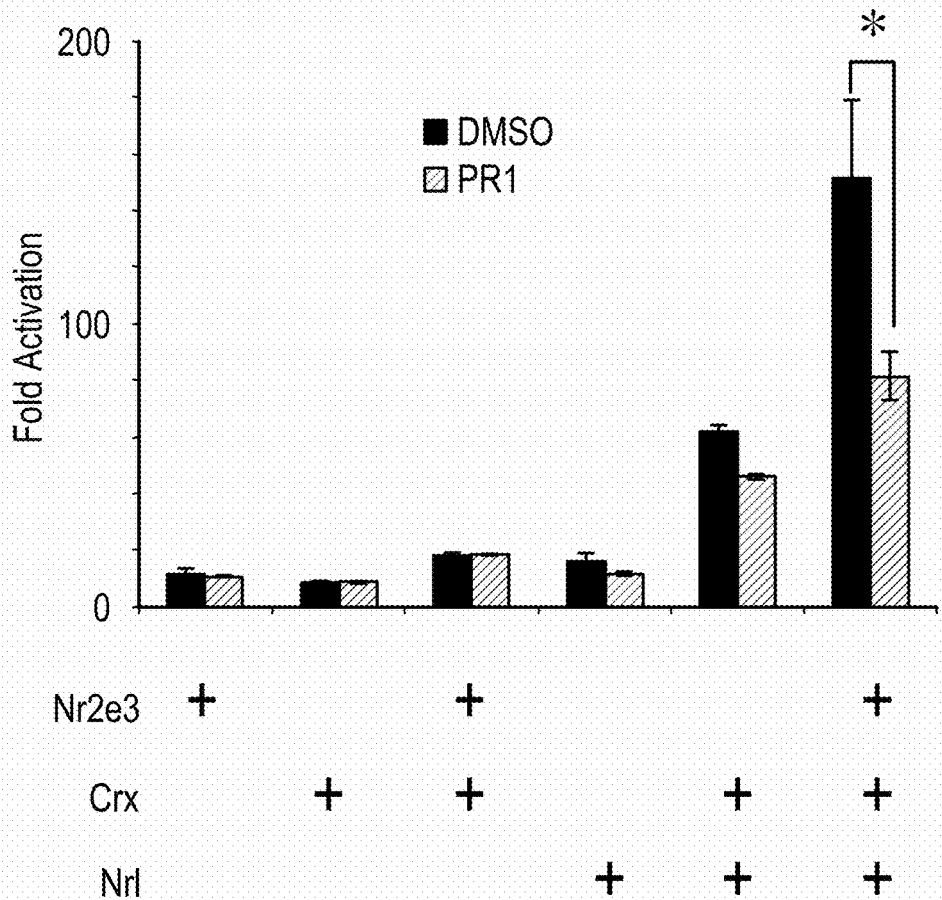

Nr2e3 loss-of-function mutations lead to a reduction in rod gene expression. To determine whether the same was true for PR1 (FIG. 6D), explant cultures of P12 retina as above were treated and assayed for other rod photoreceptor genes. After 2 days in culture, PR1 decreased the expression of the rod specific genes Nrl, Nr2e3, Rho, Gnat1, and Pde6b compared to DMSO treatment by qPCR analysis (FIG. 6C). However, PR1 did not significantly decrease the expression of Gnb1 or Crx, suggesting that PR1 was not causing a general loss of photoreceptors. To determine the dose-response relationship between PR1 concentration and expression of rod genes, retinas from P12 mice were explanted in media containing DMSO or 0.1, 1, 5, or 10 µM PR1 for 2-3 days and assayed Nrl, Nr2e3, and Rho expression by qPCR. Some effect of PR1 at a concentration as low as 0.1 uM was observed for all three rod genes tested, but statistically significant reductions were observed with the higher concentrations (FIG. 6E). PR1 was tested to determine whether it could cause a reduction in Rho expression in human rod photoreceptors as well. Pairs of 113 day post-conception retinas were explanted in media with DMSO or 10 µM PR1 for 7 or 23 days. After 7 and 23 days in culture, PR1 decreased the expression of Rho compared to DMSO treatment (FIG. 6F), similar to the effect observed in mouse retinal explants.

Nr2e3, Crx, and Nrl are known to activate rod gene expression by forming a complex at the promoters of rod genes. To test whether PR1 might interfere with this complex, a luciferase reporter assay was used. For this assay, the rhodopsin promoter driving firefly luciferase was co-transfected with Nrl, Nr2e3, or Crx or all of these transcription factors together into HEK293T cells. A large synergy in the activation of the rhodopsin reporter was found with the combination of these three transcription factors (FIG. 6G). When PR1 was added to the cells, a large reduction in the activation of the rhodopsin promoter reporter was observed after transfection with all three factors or with Crx and Nrl (FIG. 6G).

Effects of PR1 on Developing Retina

Loss-of-function mutations in Nr2e3 cause an increase in the number of S-opsin+ photoreceptors and a decrease in rhodopsin expression. To determine whether PR1 has similar effects on developing photoreceptors, retinas from P0 mice were explanted in media containing DMSO or 1 µM PR1 and assessed the level of rod genes with Western blots and qPCR after two to five days in vitro (FIG. 7A). When the P0 retina explants were analyzed by Western blot, those treated with PR1 expressed less rhodopsin protein than DMSO controls (FIGS. 7B and 7C). Expression of additional genes was tested using qPCR. After 2 days in culture PR1 decreased the expression of the rod specific genes Nrl, Nr2e3, Rho, and Gnat1 compared to DMSO (FIG. 7D). However, PR1 did not significantly decrease the expression of Gnb1, Crx, or Otx2, suggesting that PR1 was not causing a general loss of photoreceptors. Immunohistochemical analysis of sections of the explants were carried out, and observed an almost complete absence of rhodopsin immunoreactivity in the PR1 treated explants (FIG. 7E). Interestingly, PR1 treatment increased the expression of the cone gene, Thrb (FIG. 7D) by qPCR, and there was an overall increase in the level of S opsin immunoreactvity in sectioned explants treated with PR1 (FIG. 7E, inset) when compared with DMSO treated control retinal explants.

Figure 7F:
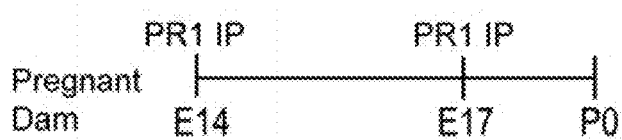
Figure 7G:
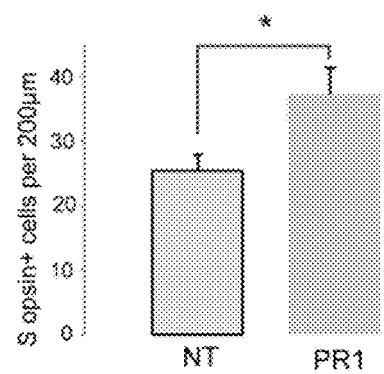
Figure 7H:
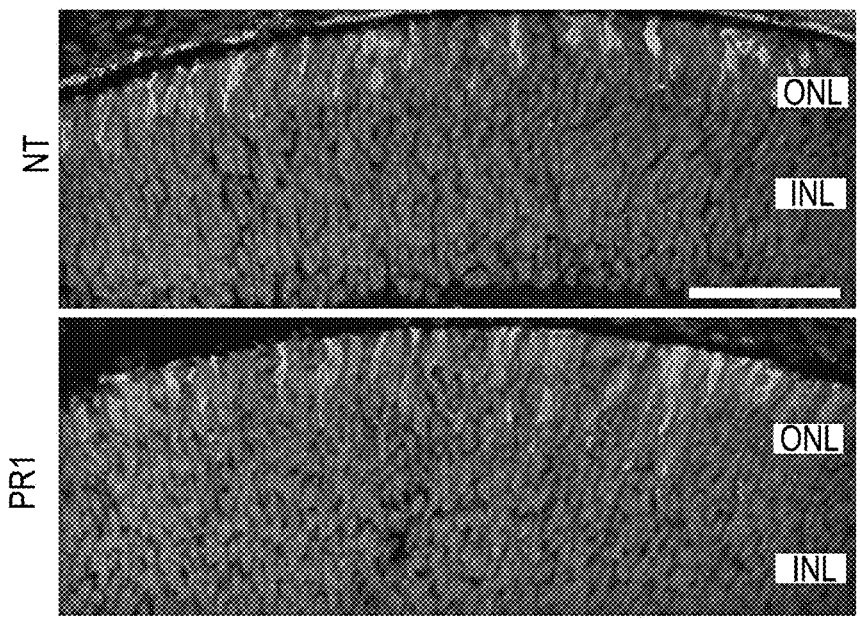
Figure 7I:
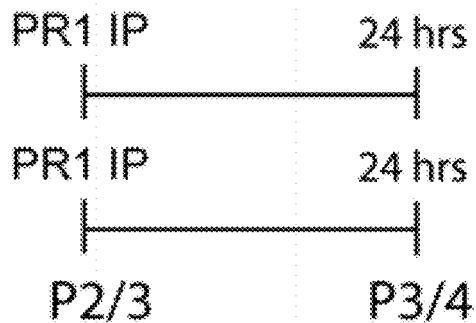
Figure 7J:
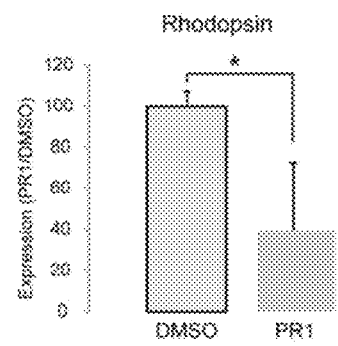

Nr2e3 is expressed in developing rods prior to birth, and so to test whether PR1 could affect prenatal rod development, wild type timed-pregnant dams were injected with 100 µl of 50 mM PR1 at E14 and E17, during peak S cone photoreceptor genesis and the onset of Nr2e3 expression (FIG. 7F). The pups were sacrificed at P0 and their retinas collected for staining and for quantifying S opsin+ photoreceptors. Pups born from the PR1-injected dams were found to have an increase in the number of S opsin-positive cells when compared with controls (FIGS. 7G and 7H). To determine if PR1 affected rhodopsin expression in developing rods in vivo, pups were injected with 20 µl of 50 mM PR1 or an equal volume of DMSO at P2 or P3 (FIG. 7I). The pups were sacrificed the following day and analyzed rhodopsin expression by qPCR. Pups intraperitoneally (IP) injected with PR1 had decreased rhodopsin compared to pups injected with DMSO (FIG. 7J). Together these results show that PR1 affects S opsin and rhodopsin in developing retina like an Nr2e3 loss-of-function mutation.

Effects of PR1 at Later Stages of Retinal Development

Figure 8A:
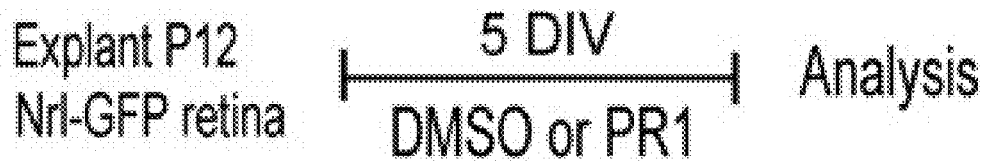
FIGS. 8A-8F. Schematic for experimental design for panels B-D (8A). Retinas from P12 Nrl-eGFP mice were explanted in DMSO or 1 µM PR1 for 5 DIV; staining for GFP (Nrl), rhodopsin and S opsin in P12 explants from Nrl-eGFP mice demonstrate a decrease in rhodopsin expression and an increase in S opsin+ cells in PR1-treated retinas; scale bar represents 50 µm (8B). PR1-treated retinas had more S opsin cells than DMSO controls per 200 µm of central retina (n=3, *p<0.05, Student's t-test) (8C). Quantification of bipolar cells (PKCα, Chx10), amacrine cells (HuCD), and Muller glia (Sox2) revealed no difference in the number of these cells (n=3; p>0.05, Student's t-test); however, the migration of Sox2+ Muller glia into the ONL of PR1-treated retinas was observed (arrow) (8D). EdU staining in DMSO and PR1 retinal explants from P12 mice for 5 DIV (8E). PR1 retinal explants had more EdU+ cells than DMSO controls (n=4, *p<0.05, Student's t-test); scale bars in 8D and 8E represent 50 µm (8F).
Figure 8B:
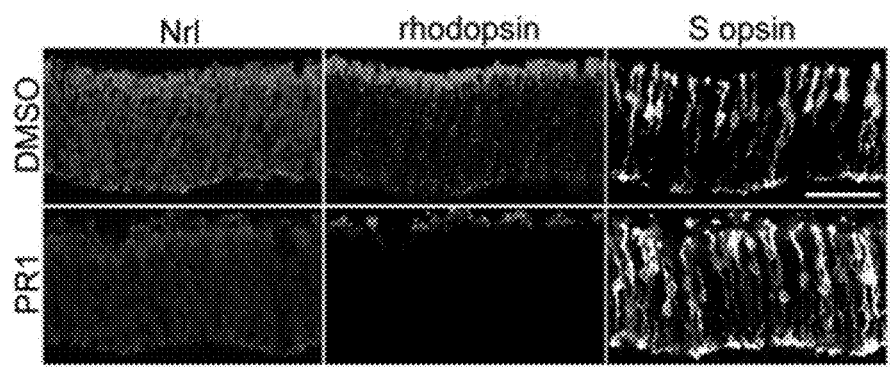
Figure 8C:
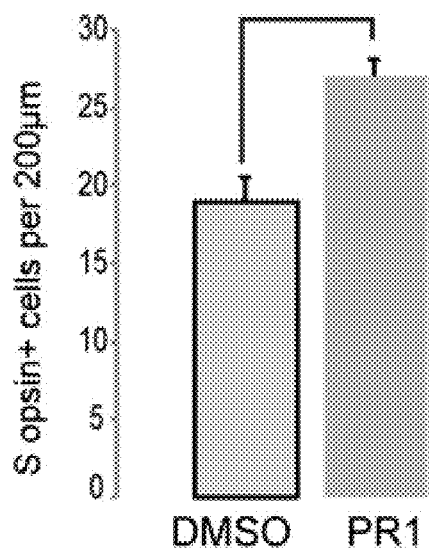

Previous loss of function genetic data has shown that Nr2e3 is required for rod photoreceptor development, but it is not known whether there is a continuing requirement for Nr2e3 in mature rods. The results from the studies of retinal explants at P12 described herein suggest a continuing role for Nr2e3 in rhodopsin expression (FIGS. 6C and 6E). To further examine the effects of PR1 at these late developmental stages, the effects of PR1 on P12 retinal explants by immunohistochemical analysis were studied (FIG. 8A). Explants from P12 Nrl-eGFP mice were cultured for 5 days in either DMSO or 1 µM PR1 containing media, and then fixed and processed for immunofluorescent labeling with anti-rhodopsin and anti-S opsin antibodies. The PR1-treated explants showed a dramatic decrease in rhodopsin staining in Nrl-GFP-positive rods. An increase in the number of S opsin+ cells in the ONL was also observed (FIGS. 8B and 8C). Thus, PR1 has effects on rod and cone gene expression, even at late stages of photoreceptor development, suggestive of a continued requirement for Nr2e3 in rod differentiation, after their initial cell fate commitment.

Figure 8D:
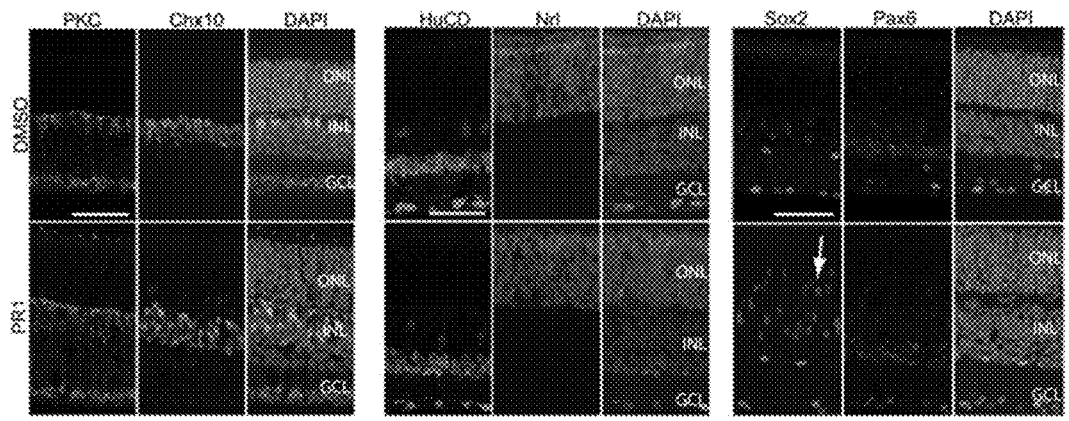
Figure 8E:
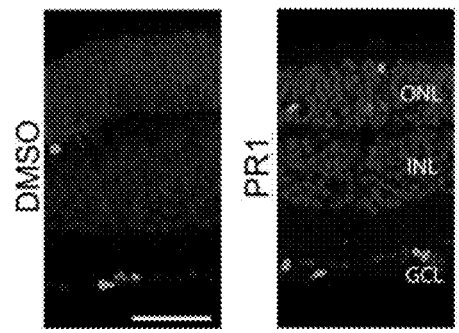
Figure 8F:
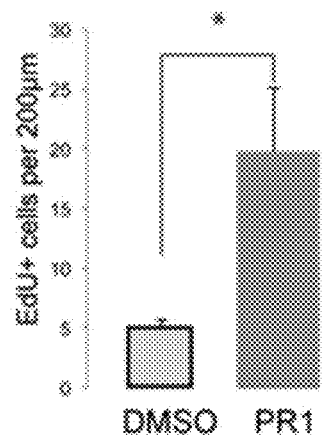

To determine if PR1 affects retinal cells other than photoreceptors, bipolar cells (PKCα, Chx10), amacrine cells (HuCD), and Muller glia (Sox2) were quantified in explants treated with DMSO or 1 µM PR1 for 5 DIV. No differences in the appearance of these other types of neurons were found between the DMSO and PR1 treated retinas. However, an increase in the migration of the Muller glial (Sox2+) nuclei into the ONL in the treated retinas was consistently observed (FIG. 8D). Previous studies have also suggested that loss of Nr2e3 leads to an increase in cone progenitor proliferation, and this might explain the increase in cones observed in the mutant. EdU (5-ethynyl-2'-deoxyuridine) was added to the cultures to determine whether PR1 might have a similar effect. Although there was an increase in the number of EdU labeled cells in the PR1 treated explants, the number of labeled cells was small overall and could not account for PR1's large effects on photoreceptor gene expression. Based on the immunohistochemical data, PR1 does not cause other widespread changes in other cell types in the retina.

PR1 Reduces Rhodopsin Expression in the Retinas of Adult Mice

Conditional deletion of Nr2e3 in mature photoreceptors has not been reported; however, deletion of Nrl in mature photoreceptors leads to a partial "reprogramming" of the rods: the cells have reduced rod gene expression and an increase in the expression of some cone genes. Because PR1 reduces rod gene expression, including Nrl, in rods even at late stages in their development (P12), it was postulated that PR1 might have similar effects in the retinas of adult mice. To determine if PR1 affects adult photoreceptor gene expression in vivo, intravitreal injections in one eye of an adult mouse (>P21) were made and compared expression to the other eye. It was found that two intravitreal injections of PR1, made over a four day period (FIG. 9A), decreased the expression of Rho mRNA assessed by qPCR (FIG. 9B) and protein, by Western blot analysis (FIGS. 9C and 9D). Interestingly, PR1 increased the expression of the cone photoreceptor marker TRβ2 in adult retinas, although an increase in S opsin at this age was not observed.

PR1 Slows Degeneration of Rods in Rhodopsin$^{P23H}$ Retinas

Figure 9E:
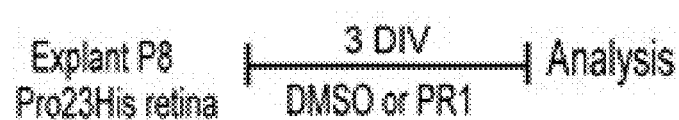
Figure 9F:
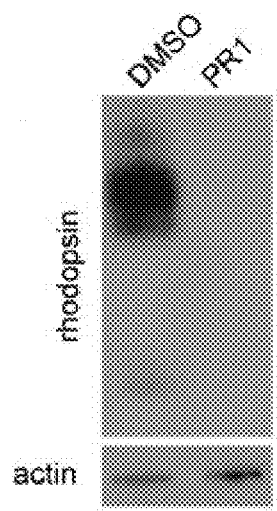
Figure 9G:
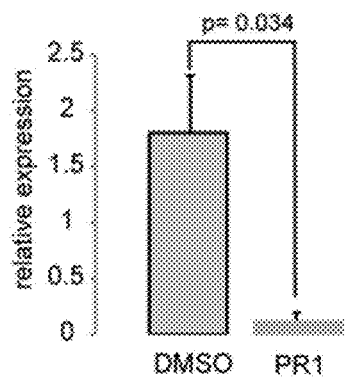

The effect of PR1 on Rho expression in adult rods might have potential as a way to slow the degeneration of these cells in dominant forms of retinitis pigmentosa, like Rho$^{P23H}$. In this disease, the affected individuals express a mutant form of rhodopsin that is likely inappropriately processed and ultimately leads to the death of the rods. To test whether reducing rhodopsin expression with PR1 might slow the degeneration of these cells, retina from Rho$^{P23H}$ transgenic mice at P8 were explanted in media containing DMSO or 2 µM PR1 and maintained the explants for three days (FIG. 9E). It was found that PR1 effectively reduced rhodopsin expression in the mutant rods (FIGS. 9F and 9G), similar to what occurs in the wild type retina. The majority of rod cell death in the Rho$^{P23H}$ transgenic line occurs between P14 and P21. Therefore, explants of retinas from Rho$^{P23H}$ mice at P12 were made and treated the explants with 1 µM PR1 or DMSO (FIG. 9H). After 6 days in vitro, the retinas were processed for histology. The number of nuclei were counted in the ONL of each retina in the central region 100 µm from the optic nerve head. PR1-treated retinas were found to have on average nearly twice the number of rod photoreceptors in the ONL than DMSO treated controls (FIGS. 9I and 9J). Gnb1 expression was also monitored as another measure of rod photoreceptor preservation because this is not directly affected by PR1 and thus serves as a surrogate for rod number. The PR1 treated explants had significantly more Gnb1 expression than the sister cultures treated with DMSO (FIG. 9K).

The studies described herein provide the first demonstration of small molecule repression of rod gene expression for the potential treatment of dominant retinitis pigmentosa. The expression of Crx, Otx2, Nrl, and Nr2e3 in mature rods is consistent with their role in the maintenance of proper photoreceptor gene expression and homeostasis. By screening compounds on rod gene expression in intact retina in vitro, a subset of compounds was found that inhibited the expression of rhodopsin in the screen. PR1 was found to inhibit expression of rod genes in developing and mature rod photoreceptors. The activity of PR1 on rod photoreceptors phenocopies loss-of-function mutations in Nr2e3, and significantly reduces expression from the rhodopsin promoter in HEK293T cells transfected with Nr2e3, Crx and Nrl. Together the data supports the conclusion that PR1 directly interacts with Nr2e3 and acts to antagonize its activity.

The primary effect observe after treatment of the retina, either in vitro or in vivo, is a reduction in the expression of rod photoreceptor specific genes, like Rho, Gnat1, and Pde6b. However, not all rod genes are reduced to the same extent; no changes in Gnb1 expression for example. Moreover, both Nrl and Nr2e3 are significantly reduced by PR1 treatment at either P0 or P12, and some of the effects observed on rod gene expression may be due to the reduction in these transcription factors. Similar results are seen after conditional knockout of Nrl in adult mice, in that rod genes are more affected than cone genes. Additionally, fewer cone genes are upregulated following knockout in the adult compared to germline knockout of Nrl, possibly due to developmental changes in the methylation status of cone gene promoters. Nonetheless, this partial "reprogramming" via conditional knockout of Nrl is sufficient to prevent photoreceptor degeneration in the Rho knockout model of RP, similar to findings with the Rho$^{P23H}$ model in vitro. Together, these studies demonstrate that downregulation of rod gene program in degenerative diseases that primarily affect rods may be an effective strategy for treatment in humans. Suppression of rhodopsin or other commonly mutated rod genes with siRNAs may also be similarly effective.

Interestingly, PR1's effects on rod gene expression are much more pronounced than the effects reported from Nr2e3 loss-of-function models, such as the Rd7 mouse and the targeted knockout of Nr2e3. In these mice, rod genes like Rho and Gnat1 are only modestly reduced, while we observed large changes with PR1 treatment. This difference may be due to our finding that PR1 also decreases the expression of Nrl, while these genetic mutations do not, and Nrl may be sufficient to drive rod gene expression in the absence of Nr2e3. In addition to changes in the expression of rod genes, Rd7 mice show a derepression of cone genes. Similarly, mutations in Nr2e3 can cause enhanced S-cone syndrome and patients present increased sensitivity to blue light. Large increases in S-opsin expression that were expected from antagonism of Nr2e3, particularly in the mature retina, were not observed. It is possible that PR1 selectively affects the ability of Nr2e3 to act as a transcriptional activator (inhibiting its ability to form a complex with Crx and Nrl), but has less of an effect on its repressor functions. However, it is also possible that acute loss of Nr2e3 has different effects than developmental deletions.

The studies described herein demonstrate that small molecules can regulate rhodopsin gene expression in developing and mature retina, and provide a novel approach to the treatment of dominant forms of RP. The ability to modulate rod and cone gene expression may also have utility in recessive forms of the disease, because conditional deletion of Nrl in mature mice provided rod protection in the Rho$^{-/-}$.

Materials and Methods

Animals

C57Bl/6 (Jackson Stock No: 000664), Rho$^{P23H}$ (Jackson Stock No: 017628) and Nrl-eGFP (Jackson Stock No: 021232) mice were used at the indicated ages. All mice were housed by the Department of Comparative Medicine at the University of Washington and protocols were approved by the University of Washington Institutional Animal Care and Use Committee.

Small Molecules

Photoregulin1 and analogs were identified by searching previous small molecule screens with SciFinder for Nr2e3 interacting molecules. All of the putative Nr2e3 interacting molecules specifically identified herein were obtained commercially from ChemDiv (San Diego, Calif.).

Retinal Explant Cultures

Intact retinas without RPE from mice of various strains and ages as indicated were explanted on 0.4 µm pore tissue culture inserts (Millipore) as previously described (Ueki, Y., et al., P53 is required for the developmental restriction in Muller glial proliferation in mouse retina. Glia, 2012. 60(10): p. 1579-89; Ueki, Y., et al., A transient wave of BMP signaling in the retina is necessary for Muller glial differentiation. Development, 2015. 142(3): p. 533-43. Full media (DMEM/F12 (1:1) containing 1% dialyzed FBS, 1% Pen Strep, 0.3% D+ glucose, 2% B27, and 1% N2) changes were performed every other day and small molecules were used at 0.1 µM to 10 µM. Where indicated, EdU (Invitrogen) was included in the media at 5 µg/mL and visualized by staining with the Click-iT EdU Alexa Fluor kit (Thermo Fisher Scientific). For human retinal explant cultures, tissue from 113 day post-conception fetuses was obtained from the University of Washington Birth Defects Laboratory and explanted on 0.4 µm pore tissue culture inserts (Millipore) in media (Neurobasal A with 1% FBS, 1% Pen Strep, 1% N2, 1% B27) containing 10 µM Photoregulin1 or an equal volume of DMSO.

Quantitative Real-Time PCR

RNA was isolated using TRIzol (Invitrogen) and cDNA was synthesized using the iScript cDNA synthesis kit (Bio-Rad) following an intervening DNase treatment with RQ1 RNase-free DNase (Promega). SSO Fast (Bio-Rad) was used for quantitative real-time PCR. For analysis, values were normalized to Gapdh and ΔΔCt between DMSO and compound-treated samples was expressed as percent of DMSO treated controls (100*2^ΔΔCt). Two-way Student's t-tests were performed on ΔCt values.

Immunofluorescence

Retinal explants or eyecups were fixed in 4% PFA in 1×PBS for 20 minutes at room temperature and then cryoprotected in 30% sucrose in 1×PBS overnight at 4° C. Samples were embedded in OCT (Sakura Finetek), frozen on dry ice, and then sectioned at 14-16 µm on a cryostat (Leica). Slides were blocked with a solution containing 10% Normal Horse Serum (Vector Labs) and 0.5% Triton X-100 (Sigma-Aldrich) in 1×PBS for 1 hour at room temperature and then stained overnight at 4° C. with primary antibodies diluted in blocking solution. Slides were washed three times with 1×PBS the following day and then incubated in secondary antibodies (Life Technologies) diluted in blocking solution for 2 hours at room temperature, stained with DAPI (Sigma-Aldrich), washed, and coverslipped using Fluoromount-G (SouthernBiotech). An Olympus FluoView FV1000 was used for confocal microscopy.

Western Blots

Retinal explants or retinas were homogenized in lysis buffer (50 mM Tris, 100 mM NaCl, 5 mM EDTA, 0.1% SDS, 1% Triton X-100, 2.5% glycerol, and 1× protease inhibitor cocktail) and equal amounts of protein samples were loaded and run in a 4-20% SDS gel (Bio-Rad). Protein was transferred to a PVDF membrane (Thermo Fisher Scientific), blocked (5% BSA and 0.1% Tween 20 in 1×PBS) and stained with primary antibodies (Supplemental Table S2) and then HRP-conjugated secondaries (Bio-Rad) diluted in blocking solution. Signals were visualized on X-ray film with SuperSignal West Dura Extended Duration Substrate (Thermo Fisher Scientific) and quantified using ImageJ software (NIH).

Dual Luciferase Assay

HEK293T cells were transfected with 1 µg of the luciferase reporter BR-225Luc, 1 ng of the control pRL-CMV (Promega) and 100 ng of hNRL-pCMVSport6 (Open Biosystems), hCRX-pCMVSport6 (Open Biosystems), or hNR2E3-pcDNA3.1/HisC in 24 well plates using Lipofectamine 3000 reagent (Thermo Fisher Scientific). Transfection reagents were removed the following day and replaced with media containing DMSO or 10 µM PR1 for 2 days. Cells were lysed and firefly and *renilla* luciferase activity was measured with the Dual-Luciferase Reporter Assay System (Promega) using a 1420 Multilabel Victor3V plate reader.

Injections

For intravitreal injections, adult mice (>P21) were anesthetized with isoflurane and injected with 1.5 µl of 10 mM PR1 using a 32-gauge Hamilton needle. Postnatal pups were injected intraperitoneally (IP) with 20 µl of 50 mM PR1 or 20 µl of DMSO at P2 or P3 with a 32-gauge Hamilton needle. Timed-pregnant dams were injected IP with 100 µl of 50 mM PR1 at E14 and E17 with a BD insulin syringe.

While illustrative embodiments have been illustrated and described, it will be appreciated that various changes can be made therein without departing from the spirit and scope of the invention.

The invention claimed is:

1. A method for decreasing rhodopsin expression in a retina, comprising treating a retina with a compound having formula (I):

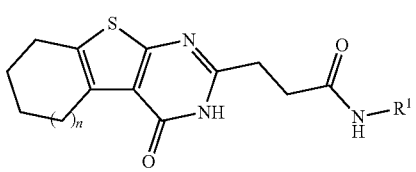
(I)

or a pharmaceutically acceptable salt thereof,
wherein $R^1$ is phenyl substituted with one or two groups independently selected from the group consisting of C1-C6 alkyl and halogen, and n is 0 or 1.

2. The method of claim 1, wherein the compound is

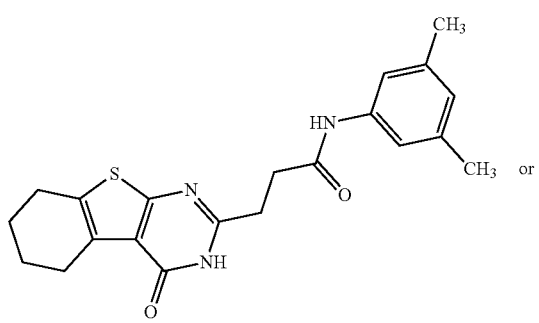

3. A method of treating a retinal disease in a subject, comprising administering to a subject in need thereof a therapeutically effective amount of a compound having formula (I):

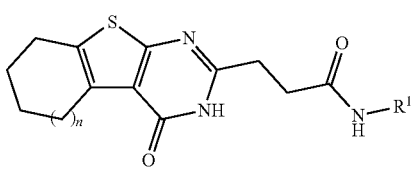
(I)

or a pharmaceutically acceptable salt thereof,
wherein $R^1$ is phenyl substituted with one or two groups independently selected from the group consisting of C1-C6 alkyl and halogen, and n is 0 or 1,
wherein the retinal disease is selected from the group consisting of retinitis pigmentosa, retinal degeneration, macular degeneration, age-related macular degeneration, Stargardt's macular dystrophy, retinal dystrophy, Sorsby's fundus dystrophy, diabetic retinopathy, diabetic maculopathy, retinopathy of prematurity, and ischemia reperfusion related retinal injury.

4. The method of claim 3, wherein the compound is

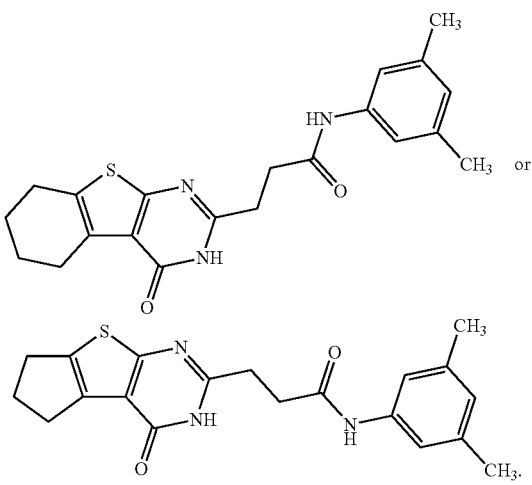

5. The method of claim 3, wherein the retinal disease is retinitis pigmentosa.
6. The method of claim 3, wherein the subject is a human.
7. The method of claim 3, wherein the administering the compound comprises systemic administration or intravitreal injection.
8. A method for decreasing rhodopsin expression in a retina, comprising treating a retina with a compound having formula (II):

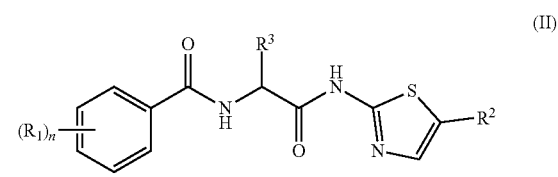
(II)

or a pharmaceutically acceptable salt thereof,
wherein $R^1$ is independently at each position a C1-C6 alkyl group, $R^2$ is selected from the group consisting of hydrogen and C1-C6 alkyl, $R^3$ is selected from the group consisting of hydrogen and C1-C6 alkyl, and n is 0, 1, or 2.

9. The method of claim 8, wherein the compound is

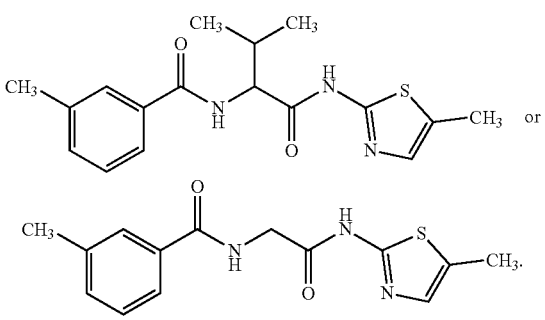

10. A method of treating a retinal disease in a subject, comprising administering to a subject in need thereof a therapeutically effective amount of a compound having formula (II):

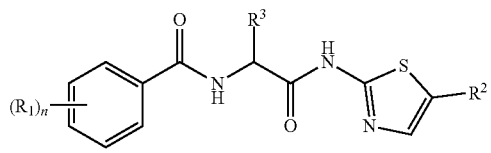

(II)

or a pharmaceutically acceptable salt thereof,
wherein $R^1$ is independently at each position a C1-C6 alkyl group, $R^2$ is selected from the group consisting of hydrogen and C1-C6 alkyl, $R^3$ is selected from the group consisting of hydrogen and C1-C6 alkyl, and n is 0, 1, or wherein the retinal disease is selected from the group consisting of retinitis pigmentosa, retinal degeneration, macular degeneration, age-related macular degeneration, Stargardt's macular dystrophy, retinal dystrophy, Sorsby's fundus dystrophy, diabetic retinopathy, diabetic maculopathy, retinopathy of prematurity, and ischemia reperfusion related retinal injury.

11. The method of claim 10, wherein the compound is

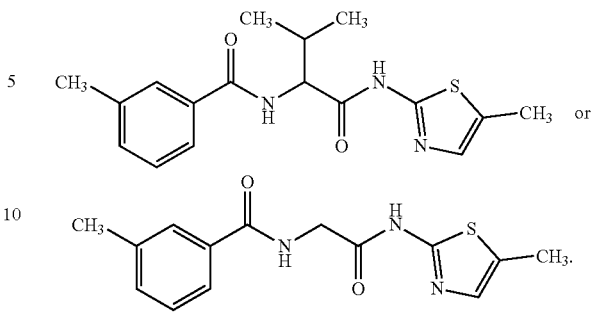

12. The method of claim 10, wherein the retinal disease is retinitis pigmentosa.

13. The method of claim 10, wherein the subject is a human.

14. The method of claim 10, wherein the administering the compound comprises systemic administration or intravitreal injection.

* * * * *

UNITED STATES PATENT AND TRADEMARK OFFICE
CERTIFICATE OF CORRECTION

PATENT NO. : 10,849,904 B2  
APPLICATION NO. : 16/447764  
DATED : December 1, 2020  
INVENTOR(S) : T. Reh et al.

Page 1 of 1

It is certified that error appears in the above-identified patent and that said Letters Patent is hereby corrected as shown below:

On the Title Page

| Column | Line | |
|---|---|---|
| 1 | 15 | Item (73) change "Teatamentary" to -- Testamentary -- |

In the Claims

| Column | Line | |
|---|---|---|
| 19 | 15 | Change "0, 1, or" to -- 0, 1, or 2, -- |

Signed and Sealed this  
Twenty-fifth Day of January, 2022

Drew Hirshfeld  
*Performing the Functions and Duties of the*  
*Under Secretary of Commerce for Intellectual Property and*  
*Director of the United States Patent and Trademark Office*